(12) United States Patent
Gollier et al.

(10) Patent No.: US 7,582,486 B2
(45) Date of Patent: Sep. 1, 2009

(54) DOUBLE RESONANCE INTERROGATION OF GRATING-COUPLED WAVEGUIDES

(75) Inventors: Jacques Gollier, Painted Post, NY (US); Eric J. Mozdy, Elmira, NY (US); Garrett A. Piech, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 311 days.

(21) Appl. No.: 11/820,068

(22) Filed: Jun. 18, 2007

(65) Prior Publication Data

US 2008/0158570 A1   Jul. 3, 2008

Related U.S. Application Data

(62) Division of application No. 10/676,352, filed on Sep. 30, 2003, now abandoned.

(51) Int. Cl.
*G01N 33/543* (2006.01)
(52) U.S. Cl. ............ 436/164; 385/12; 422/82.11; 436/518; 436/524; 436/805
(58) Field of Classification Search .............. None
See application file for complete search history.

(56) References Cited

U.S. PATENT DOCUMENTS

| | | | |
|---|---|---|---|
| 4,755,667 A | 7/1988 | Marsoner et al. | 250/227 |
| 5,712,705 A | 1/1998 | Fattinger et al. | 356/354 |
| 6,455,004 B1 | 9/2002 | Tiefenthaler | 422/91 |
| 6,600,563 B1 | 7/2003 | Bahatt et al. | 356/445 |
| 6,628,376 B1 | 9/2003 | Nikitin et al. | 356/38 |
| 6,707,561 B1 | 3/2004 | Budach et al. | 356/521 |
| 7,094,595 B2 | 8/2006 | Cunningham et al. | 435/287.2 |
| 7,118,710 B2 | 10/2006 | Cunningham | 422/82.09 |
| 2002/0127565 A1 | 9/2002 | Cunningham et al. | 435/6 |
| 2002/0128234 A1 | 9/2002 | Hubbell et al. | 514/100 |
| 2002/0168295 A1 | 11/2002 | Cunningham et al. | 422/82.05 |
| 2003/0017580 A1 | 1/2003 | Cunningham et al. | 435/287.2 |
| 2003/0017581 A1 | 1/2003 | Li et al. | 435/287.2 |
| 2003/0026891 A1 | 2/2003 | Qiu et al. | 427/58 |
| 2003/0027327 A1 | 2/2003 | Cunningham et al. | 435/287.2 |
| 2003/0027328 A1 | 2/2003 | Cunningham et al. | 435/287.2 |
| 2003/0032039 A1 | 2/2003 | Cunningham et al. | 435/6 |
| 2003/0054378 A1 | 3/2003 | Karube et al. | 435/6 |
| 2003/0059855 A1 | 3/2003 | Cunningham et al. | 435/7.9 |
| 2003/0068657 A1 | 4/2003 | Lin et al. | 435/7.9 |
| 2003/0077660 A1 | 4/2003 | Pien et al. | 435/7.1 |
| 2003/0092075 A1 | 5/2003 | Pepper | 435/7.9 |
| 2003/0113766 A1 | 6/2003 | Pepper et al. | 435/6 |

(Continued)

FOREIGN PATENT DOCUMENTS

WO    WO 99/30135    6/1999

(Continued)

*Primary Examiner*—Christopher L Chin
(74) *Attorney, Agent, or Firm*—John L. Haack; Thomas R. Beall

(57) ABSTRACT

A method for using a double resonance effect within a grating-coupled waveguide (GCW) sensor, as generated from a light beam with a given span of wavelengths or angles, is provided. The method can be used for label-independent detection of biological and chemical agents, to interrogate biological-binding events or chemical reactions within a sensing region at increased sensitivity, and with decreased sensitivity to environmental perturbations. Also described is an optical interrogation system incorporating the method.

12 Claims, 16 Drawing Sheets

U.S. PATENT DOCUMENTS

| | | | |
|---|---|---|---|
| 2003/0133640 A1 | 7/2003 | Tiefenthaler | 385/12 |
| 2004/0132172 A1 | 7/2004 | Cunningham et al. | 435/287.2 |
| 2004/0132214 A1 | 7/2004 | Lin et al. | 436/518 |
| 2004/0151626 A1 | 8/2004 | Cunningham et al. | 422/58 |
| 2004/0223881 A1 | 11/2004 | Cunningham et al. | 422/82.05 |

FOREIGN PATENT DOCUMENTS

| | | |
|---|---|---|
| WO | WO 99/31275 | 6/1999 |
| WO | WO 01/40757 | 6/2001 |

FIG. 11A                FIG. 11B
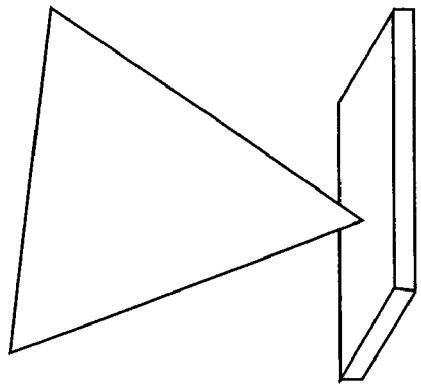 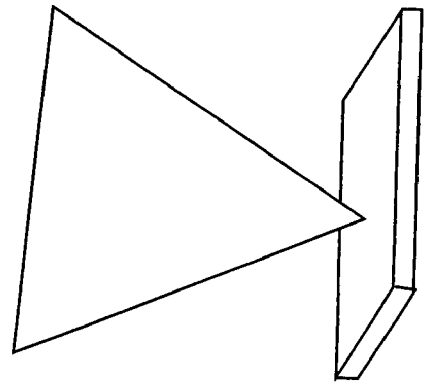
FIG. 12
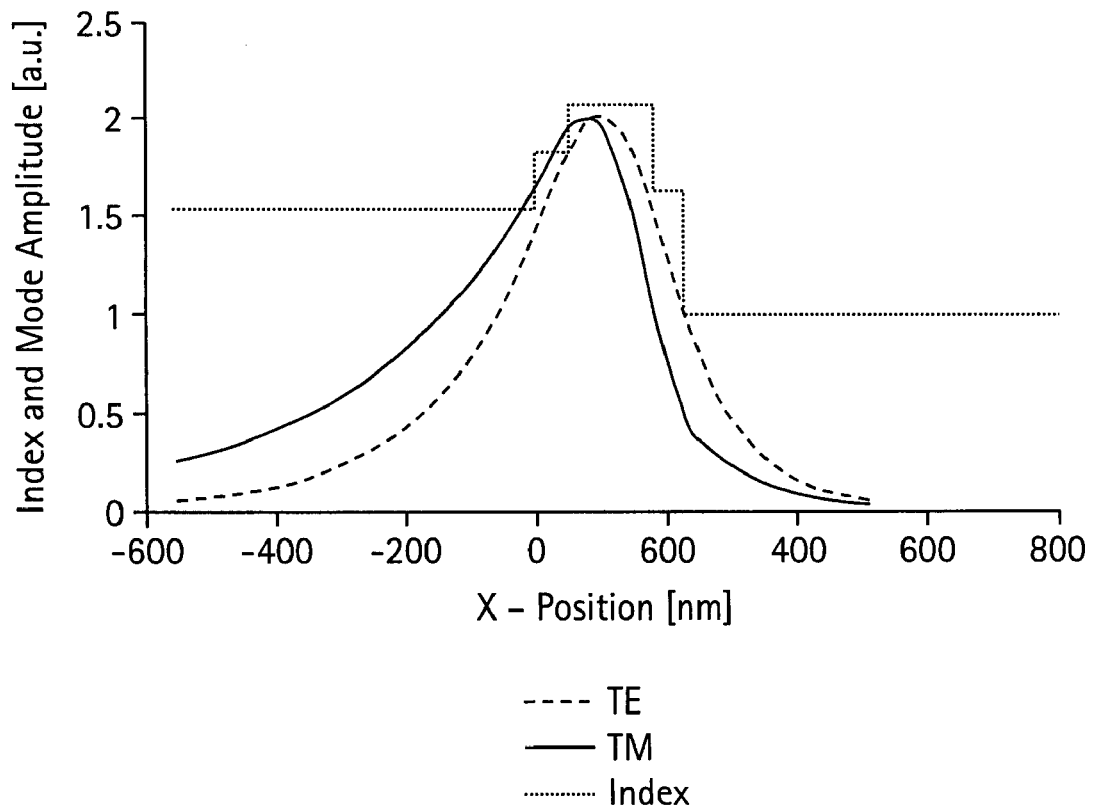

DOUBLE RESONANCE INTERROGATION OF GRATING-COUPLED WAVEGUIDES

CROSS REFERENCE TO RELATED APPLICATION

This application is a divisional application of U.S. patent application Ser. No. 10/676,352, filed Sep. 30, 2003, now abandoned.

FIELD OF INVENTION

The present invention pertains in general to a sensor used for label-independent detection of biological and chemical agents. More particularly, the invention relates to 1) a method for using a double resonance effect within a grating-coupled waveguide (GCW) sensor, as generated from a light beam with a given span of wavelengths or angles, to interrogate biological-binding events or chemical reactions within a sensing region at increased sensitivity, and with decreased sensitivity to environmental perturbations, and 2) an optical interrogation system incorporating the method.

BACKGROUND

Evanescent field-based sensors are fast becoming a technology of choice for accurate label-free detection of a biological, biochemical, or chemical substance (e.g., cells, spores, biological or drug molecules, or chemical compounds). This technology typically involves using a grating-coupled waveguide (GCW) to sense a concentration change, surface adsorption, reaction, or the mere presence of a biological or chemical substance at the waveguide surface. These detectable events are manifested as a change in the effective refractive index of a waveguide mode that partially or completely overlaps the sensing region (waveguide substrate). To generate the evanescent or optical field, an optical interrogation system uses optical elements, such as a grating or prism, to couple a light beam from a light source in and out of an optical mode in the waveguide of the GCW sensor. The optical interrogation system also includes a detector that receives the light beam coupled out from the waveguide. The angle or wavelength of the emitted light beam is analyzed to determine the effective refractive index of the waveguide. Changes in the angle or wavelength of the probe light, for example, indicate changes of the waveguide effective index that result from activity at the sensor surface.

In determining the effective refractive index of the GCW sensor, the principles of optical-physics dictate that the light beam received by the detector had interacted with the waveguide under a resonant condition, where the wavevectors of a diffraction grating, incoming light beam, and guided mode all sum to zero, thereby allowing one to probe the effective index of the mode, which changes together with the surface index. This resonant condition occurs only for a specific wavelength and angle of the incoming light, and changes in this angle or wavelength correspond to changes in the effective refractive index of the waveguide caused by the concentration changes, surface adsorption, or reactions of biological or chemical substances in the sensing region of the GCW sensor. Thus, the optical interrogation system is used to sense a change in the effective index of the GCW sensor which enables one to determine whether or not a substance of interest is located within the sensing region of the GCW sensor.

For this technology to be viable, one must have an optical interrogation system and in particular a detector capable of accurately monitoring the resonant angle, the wavelength, or both. In particular, the optical interrogation system must emit a light beam that interacts with the GCW sensor, and must in turn receive the light beam coupled-out of the GCW sensor and process that light beam to detect in real time any changes in the resonant angle and/or wavelength of the light beam. While there are many approaches for accomplishing these tasks, each has unique challenges associated with implementation, since the light beam output from the GCW sensor may be relatively weak and the presence of multiple sources of noise can degrade the light beam, especially in high-throughput screening applications.

Evanescent- or optical-field sensors have demonstrated both high sensitivity and an ability to detect binding reactions of as little as about 250 Da molecular weight (e.g., biotin binding to streptavidin). In recent years, the biological, pharmaceutical, and other research communities have begun to recognize that optical field-based sensors can be useful, high-throughput research tools to measure a variety of biological or biochemical functions. GCW sensors are particularly attractive for use in high-throughput screening applications, where the absence of fluorescent tags and the possibility of reduced false-negatives would provide a large cost advantage. For this reason, microtiter well plates, also known as microplates, have caught the attention of researchers as a promising platform for such sensors, where 96 or 384 individual wells provide the high-throughput access demanded by the industry. When applied in the context of a microplate, the waveguide and diffraction grating of the GCW sensor are preferably located in the bottom of each well (e.g., the diffraction grating may be stamped or otherwise molded into the well bottom, and the waveguide is subsequently applied on top of the diffraction grating). The wells themselves are typically composed of an optically transparent, low-birefringence, preferably low-cost plastic that is typically about several hundreds of microns to about a few millimeters thick. Plates fabricated on glass substrates also are suitable for these applications.

In the context of a high-throughput screening application, microtiter well plates will be handled by various types of robotic instruments. During the course of robotic manipulations fluids will be added and removed from individual wells, assay protocols may require incubation periods; hence, the microplate will likely as a consequence be inserted and reinserted into the sensor or detection device more than once during a single assay measurement cycle. Since the resonance condition of the GCW sensor is critically dependent on the angle of the light striking the microplate, repositioning of the plate in the detection device will manifest itself (at least in part) in the form of angular noise in the sensor instrument. This environmental perturbation can in fact be much larger than and overwhelm the sought-after response of the GCW sensor to true biological or chemical changes in the sensing region. Thus, this problem can work at cross-purposes with a sensor that is designed purposefully to enhance or maximize sensitivity to its biochemical environment. In other words, the sensor's extra-sensitivity can exacerbate environmental background noise. The simultaneous desire for an extremely responsive sensor with high biochemical sensitivity and need for low susceptibility to environmental responses place unique constraints on the system designer. The present invention can balance these two competing requirements, and the optical interrogation system, GCW sensor, and method of the present invention successfully address and satisfy this difficult problem.

SUMMARY OF THE INVENTION

The present invention relates in part to a method for increasing the biochemical sensitivity of an evanescent- or optical-field sensor having a grating-coupled waveguide (GCW) structure, as well as decreasing its sensitivity to environmental perturbations. The method, in part, involves generating a double resonance effect by using more than one propagation direction in the waveguide of the sensor from which is derived an output signal from the sensor. One can produce a sensitivity or improved signal-to-noise ratio (SNR) of greater than that obtained from using only a single propagation direction for biological or chemical sensors of grating-coupled waveguide (GCW) systems. Moreover, appropriate use of the resonances from the separate propagation directions can also aid in mitigating angular misalignments of the GCW sensor.

Due to symmetry in the propagation direction of the waveguide, a typical sensor device can provide two reflected angles or wavelengths for a given input optical beam near normal incidence. That is, for a given angle or wavelength, two resonances can exist simultaneously in the waveguide as a result of light propagation in two different, symmetrical directions. These different signal propagation directions in the waveguide may be excited simultaneously or in sequence by the detection instrument.

With a wider field of interrogation, the two reflected resonances will display opposite directional responses to index changes in angle-space, while in wavelength-space the resonances will display similar directional responses. By detecting both resonances from an optical beam at either a given incident angle or wavelength, one can calculate or derive indirectly the signal sensitivity. The present technique takes advantage of either the arithmetic mean or the difference of the resonance modes in a detection system. The method can produce greater sensitivity than that which is obtainable using only one propagation direction. When much of the system noise on each resonance is common-mode, one can approximately double (2×) the sensitivity of the sensor to refractive index changes of a superstrate by employing the two resonances together. In the case of uncorrelated noise on each resonance, the sensitivity can be increase by a factor of about $\sqrt{2}$. In addition, because the two propagating modes are symmetric about an incidence angle of zero degrees (normal to the waveguide), one can ascertain information about the absolute angle of the GCW sensor by considering both resonances together. In a situation where the instrument monitors the resonance wavelength, the average of the two resonance signals is insensitive to angle shifts. In a situation where the detection instrument monitors the angle of the resonances, the average signal will indicate the zero angle position. Hence, the difference between the peaks also would be insensitive to angle changes. Using the correct parameter in each situation, the absolute angle of the GCW substrate (i.e., microplate) can be factored out or ignored.

Further, according to another aspect, the invention pertains to a label-independent detection system that can exploit the double resonance phenomenon. Such a system may use an evanescent- or optical-field for detecting biological or chemical agents. An evanescent- or optical-field sensor may comprises a substrate, a diffraction grating, and a waveguide film, wherein the grating and/or waveguide film form a waveguide, and an optical signal propagated in more than one direction is used to derive an output signal from the sensor. The detection system may comprise: a substrate surface having a sensing region with a bio- or chemo-responsive layer, and an optical interrogation apparatus for monitoring the bio- or chemo-responsive layer. The optical interrogation apparatus further includes a grating-coupled waveguide structure, a light source, an optical delivery system, and a detection instrument, wherein a light beam having more than one direction of propagation is used in the waveguide to generate a sensor response for either a given angle or wavelength. The detection system may further include an air-fluid delivery system, comprising either macro or micro-fluidic passages designed to deliver biological or chemical analytes to the sensing region.

Alternatively, a method for using an evanescent-field or optical-field sensor like that described for detecting biological or chemical agents comprises: providing a sensor system having a optical-field sensing region comprising a substrate surface having at least a bio- or chemo-responsive layer; generating a double resonance within a grating-coupled waveguide of said system for either a given angle or wavelength; exposing an individual sensing region to an environment with analytes; and monitoring a response from the sensor system. The substrate can be modified with one or more coatings or layers of materials with desired surface chemistry, which enhance stable immobilization of said bio- or chemo-responsive layer.

Additional features and advantageous of the present invention will be revealed in the following detailed description. Both the foregoing summary and the following detailed description and examples are merely representative of the invention, and are intended to provide an overview for understanding the invention as claimed. Reference to the accompanying figures and the following detailed description may convey a better understanding of the present invention.

BRIEF DESCRIPTION OF THE FIGURES

FIG. 7 illustrates the concept of forward and backward propagation in the GCW waveguide.

FIG. 9 shows two implementations of the optical detection system for GCW sensors.

FIG. 11 is a schematic representation of the angular misalignment of the GCW sensor under the angular interrogation instrument scheme. FIG. 11A shows an aligned sensor illuminated with a cone of light (gray region), where the double resonances appear on each side of the normal to the surface. FIG. 11B shows the effect of misalignment, where the grayed lines indicate the unaligned state; the resonances continue to appear on each side of the normal, while the normal has simply shifted relative to the input beam. The average position of the resonances has therefore shifted, but their difference is unaffected. This insensitivity scheme only applies when the angular misalignment is small compared to the total angular extent of the input beam. As this figure shows, when the tilt causes one of the resonances to move beyond the boundary of the input light cone, this resonance will no longer be excited by the optical system.

FIG. 12 depicts sample modes of a GCW structure used in the example calculation of the dispersion correction factor necessary to correctly insulate the GCW sensor from angular misalignments.

DETAILED DESCRIPTION OF THE INVENTION

Section I—Definitions

Figure 1:
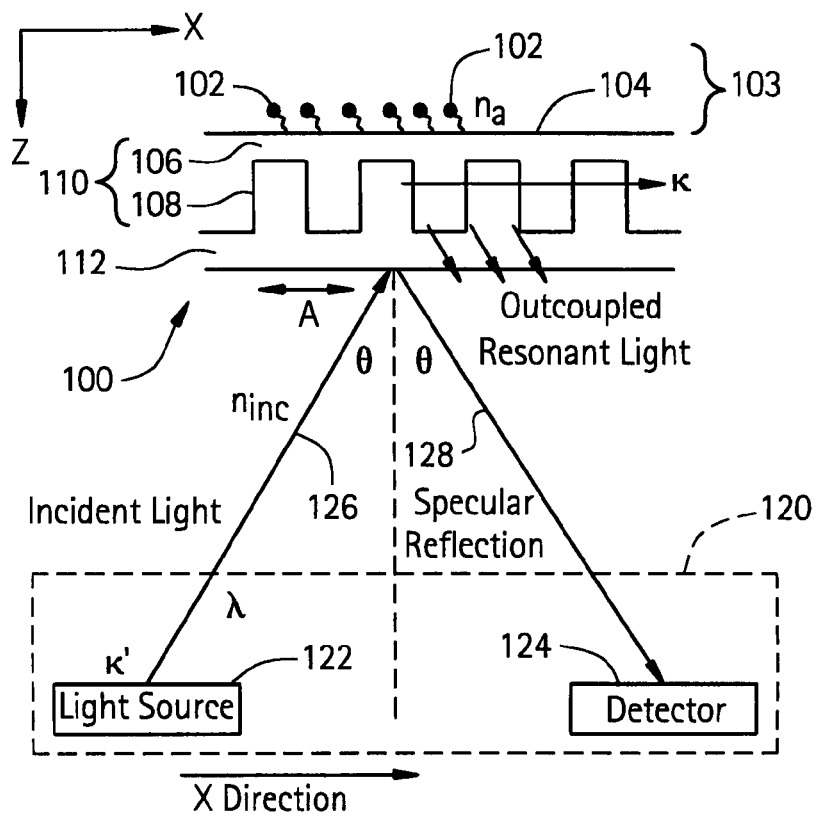
FIG. 1 is a diagram of the basic components of an optical interrogation system and GCW sensor in accordance with the present invention.

Before describing the present invention in detail, this invention is not necessarily limited to specific compositions, reagents, process steps, or equipment, as such may vary. As used in this specification and the appended claims, the singular forms "a," "an," and "the" include plural referents unless the context clearly dictates otherwise. It is also to be understood that the terminology used herein is for the purpose of describing particular embodiments only, and is not intended to be limiting. All technical and scientific terms used herein have the usual meaning conventionally understood by persons skilled in the art to which this invention pertains, unless context defines otherwise.

The term "air-fluid delivery system" as used herein refers to a fluidic (i.e., gaseous or liquid) system that can collect samples of biological or chemical analytes from the atmosphere or surrounding environs, and deliver the samples to a sensor.

The term "analyte" or "target" as used herein refers to a biological molecule or chemical entity, molecule, or compound to be detected.

The term "biological molecule" or "biomolecule" refers to any kind of biological entity, including, such as, modified or unmodified nucleotides, nucleosides, peptides, polypeptides, proteins, protein domains, fusion proteins, antibodies, membrane proteins, lipids, lipid membranes, cellular membranes, cell lysate, oligosaccharides, or polysaccharides, or lectins.

The term "bio-responsive" or "chemo-responsive" as used herein refers to the ability to adsorb, desorb, react with, or bind a biological or chemical species.

The term "bio- or chemo-responsive layer" as used herein refers to a biological or chemical species, usually coated on a top surface of a GCW sensor (in the superstrate, or sensing region, of the sensor), used to promote binding, adsorption/desorption, or reaction with the biological or chemical species to be detected.

The term "evanescent" as used herein refers to that portion of an optical field where the effective index of the optical field exceeds the local index of the medium, thereby necessitating an exponentially decaying field in space, according to Maxwell's Equations.

The term "evanescent-field sensor" or "optical-field sensor" as used herein refers generally to any kind of sensor where an evanescent or confined optical field interacts with a medium to be sensed, and changes in the refractive index or optical field can be detected to indicate properties or changing characteristics of the medium. The optical field confinement is typically accomplished with a waveguide structure, where one or both extremeties of the waveguide mode are evanescent fields.

The term "fluid" or "film of fluid" as used herein refers to a material or medium that can flow such as a gas, a liquid, or a semisolid.

The term "functionalization" as used herein relates to modification of a solid substrate to provide a plurality of functional groups on the substrate surface. The phrase "functionalized surface" as used herein refers to a substrate surface that has been modified to have a plurality of functional groups present thereon. The surface may have an amine-presenting functionality (e.g., γ-amino-propylsilane (GAPS)) coating, or may be coated with amine presenting polymers, such as chitosan or poly(ethyleneimine).

The term "microspot" refers to a discrete or defined area, locus, or spot on the surface of a substrate, containing biological or chemical probe material. The corresponding microspots are referred to as "probe microspots," and these microspots are arranged in a spatially addressable manner to form a microarray. One or more microspots, as in an array, constitute a sensing region.

The terms "nucleoside" and "nucleotide" refer to moieties which contain not only the known purine and pyrimidine bases, but also other heterocyclic bases that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. As used herein, the term "amino acid" is intended to include not only the L-, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, ε-nicotinoyl-lysine, isonipecotic acid, tetrahydroisoquinoleic acid, α-aminoisobutyric acid, sarcosine, citrulline, cysteic acid, t-butylglycine, t-butylalanine, phenylglycine, cyclohexylalanine, β-alanine, 4-aminobutyric acid, and the like.

The term "probe" refers to either a natural or synthetic molecule, which according to the nomenclature recommended by B. Phimister (*Nature Genetics* 1999, 21 supplement, pp. 1-60.), is immobilized to a substrate surface. A probe may be either a natural or synthetic, bio- or chemo-reactive molecule, which has been immobilized to a substrate surface constituting part of a sensing medium. Preferably, probes are arranged in a spatially addressable fashion to form an array of microspots. A set of probes can bind or otherwise react with analytes. Examples of probes which may be employed according to this invention may include, but are not limited to, antibodies, (e.g., monoclonal antibodies and antisera reactive with specific antigenic determinants), glycolipids including gangliosides, pharmaceutical or toxin molecules, polynucleotides, peptide nucleic acid (PNA), peptides, proteins, cofactors, lectins, polysaccharides, viruses, cells, cellular or lipid membranes, membrane immuno-receptors, and organelles. For chemical detection, the probes may include a polymer matrix, or a ligand-gated ion channel membrane. Preferably, probes are arranged in a spatially addressable manner to form an array of microspots. When the array is exposed to a sample of interest, molecules in the sample selectively and specifically binds to their binding partners (i.e., probes). The binding of a "target" to the probes occurs to an extent determined by the concentration of that "target" molecule and its affinity for a particular probe.

The term "receptor" as used herein refers to a molecule that has an affinity for a ligand. Receptors may be naturally-occurring or man-made molecules. They may be employed in their unaltered state or as aggregates with other species. Examples of receptors which may be employed according to this invention may include, but are not limited to, antibodies, monoclonal antibodies and antisera reactive with specific antigenic determinants, pharmaceutical or toxin molecules, oligonucleotides, polynucleotides, DNA, RNA, peptide nucleic acid (PNA), peptides, polypeptides, protein domains, proteins, fusion proteins, cofactors, lectins, oligosacharides, polysacharides, viruses, cells, cellular membranes, cell membrane receptors, and organelles. Receptors are sometimes referred to in the art as anti-ligands. A "ligand-receptor pair" is formed when two molecules have combined through molecular recognition to form a complex.

The term "sample" as used herein relates to a material or mixture of materials, typically, although not necessarily, in fluid form, containing one or more components of interest.

The term "sensing region" as used herein refers to an area or window on a surface of an optical-field sensor where analytes may attach and be detected. Over the total surface of an optical-field sensor, there is at least one, preferably a plurality of sensing regions that may be each optically accessed in sequence or in parallel. In other words, a sensing region is analogous to a slide or a frame of film.

The term "substrate" or "substrate surface" as used herein refers to a solid or semi-solid material which can form a stable support and can function as an optical component of an optical-field sensor. The substrate surface can be selected from a variety of materials, including, for instance, glass, glass-ceramic, metals, polymers, plastics, or combinations of these.

The term "target(s)," "target moieties," "target analyte," "biological target," or "chemical target" refers to a solvated particle, molecule or compound of interest in a sample that is to be detected and identified. Suitable targets include organic and inorganic molecules, biomolecules. In a preferred embodiment, the target may be an environmental pollutant (e.g., such as pesticides, insecticides, toxins, etc); a chemical (e.g., solvents, polymers, organic materials, etc); a therapeutic molecule (e.g., therapeutic and abuse drugs, antibiotics, etc); a biomolecule (e.g., hormones, cytokines, proteins, peptides, protein domains, fusion proteins, nucleotides, oligonucleotides, DNA, RNA, peptide nucleotide acids (PNA), genomic DNA, lipids, lipid membranes, carbohydrates, cellular membrane antigens, receptors or their ligands, etc); whole cells (e.g., pathogenic bacteria, eukaryotic cells, etc); a virus; or spores, etc.

Section II—Description

The present invention pertains, in part, to a sensor, sensor system, and method of detecting analytes by means of using evanescent- or optical-field waveguides. Reference to the accompanying figures and the following detailed description may convey a better understanding of the present invention. FIG. 1 is a schematic representation of a generic optical-field sensor device. An optical confinement layer, such as a grating-coupled waveguide (GCW), provides a zone through which an optical mode propagates. A grating-coupled waveguide structure can be designed to act as a filter either in wavelength or angle-space, reflecting only a particular, resonant wavelength or angle from an input optical beam. GCWs offer good sensitivity to the surrounding environment or medium (index). Grating coupled waveguides can provide a very narrow spectral response to incident light. As a result, GCWs have been applied to a wide variety of applications, including optical filters, laser cavity mirrors, and biosensors, among others.

A light source populates a mode of the waveguide and provides the evanescent optical field that penetrates into a medium (superstrate) to be sensed. A change in the mass or refractive index of the sensing medium causes a corresponding change in the properties of the field in the optical confinement layer. In other words, as the sensor surface encounters different biological or chemical molecules, the evanescent field registers changes in response, which is manifested as a change in the effective index of the waveguide mode that can be monitored. For biosensing uses, the optical response of the GCW varies as different biological or chemical target species are brought into contact with the device. Because the evanescent field extends into the medium, some of these targets may adsorb or bind with probe materials on the surface of the sensor or otherwise interact, thereby altering the refractive index and the evanescent-field. Due to the physics of the diffraction grating (or other coupling methods), an incident or input probe light beam can be coupled into the waveguide to create this confined optical energy (i.e., waveguide mode); and likewise, the grating allows a subsequent output coupling of a light beam from the waveguide that contains the desired information. This information is typically in the form of either a change in the wavelength or angle of the output light, since interaction between the confined optical mode and the probe beam requires precise matching of the wavelength and/or angle parameters as dictated by the refraction/diffraction physics employed in either the prism, grating, dielectric stack, or etc. to extract information from the sensor. It should be noted that, while the evanescent tail is typically the portion of the of the waveguide mode that interacts with a biological sample, GCW sensors can be designed such that any portion of the mode (guided or evanescent) can overlap a sensing region. This invention applies equally to sensors that use any or all parts of the confined optical energy for sensing.

GCW devices are used directly to monitor biological or chemical assays in a label-free format, where the expense and experimental perturbations of fluorescent dyes are completely avoided. The sensitivity of the device is measured as the amount of angular (wavelength) shift the reflected beam incurs for a given cover index change. (See e.g., U.S. Pat. Nos. 6,455,004, 5,738,825, 4,952,056, or 4,815,843, to Tiefenthaler et al., the contents of which are incorporated herein by reference.)

GCWs, however, should be optimized in terms of sensitivity to biological or chemical analytes so as to enhance their functional performance. According to the present invention, we explain and describe a double resonance phenomenon, and methods for exploiting the double resonance in order to either double the sensitivity or improve the signal-to-noise of biological sensors. The method improves instrument/sensor sensitivity by exploiting the optical symmetry in the waveguide design. Moreover, the double resonance can be useful to mitigate over sensitivity to undesirable perturbations, such as angular or waveguide jitter in an optical system. In other words, for a given index change, the basic symmetrical design of GCWs can promote greater sensitivity of the sensor for angular interrogation, while improving signal-to-noise ratios by filtering background signal or rejecting environmental noise.

A. Sensor Sensitivity

According to one aspect, the present invention provides an evanescent-field optical sensor for detecting chemical, biochemical or biological substances in a sample. As FIG. 1 shows, the sensor 100 includes a waveguiding structure 110 formed by a layer of material (e.g., waveguiding film) 106 covering a substrate, wherein the waveguiding film has a refractive index greater or higher than the refractive index of the substrate; a diffraction grating 108 contained in or near the waveguiding structure 110; and a bio- or chemo-responsive layer 103 covering the waveguiding film 106 in a region around the diffraction grating 108, wherein the bio- or chemo-responsive layer is capable of binding with the substances to be assayed. Preferably, the bio- or chemo-responsive layer has a thickness of less than about one wavelength. Preferably the waveguide film is made of a dielectric material such as $Ta_2O_5$, $TiO_2$, $TiO_2$—$SiO_2$, $HfO_2$, $ZrO_2$, Si, $SiO_2$, $Al_2O_3$, $Si_3N_4$, HfON, SiON, scandium oxides or mixtures thereof. The diffraction grating 108 is formed within a substrate 112 or waveguide film 106 by embossing, holography, or other methods. The diffraction grating 108 can thereby be located above, below, or even within the waveguide film 106. Moreover, a diffraction grating 108 need not be in direct physical contact with a waveguide film 106, simply near enough to cause optical influence on the waveguide mode. Furthermore, due to effective-index waveguiding, the diffraction grating itself can be fabricated with appropriately high enough index to serve as the waveguide itself without the need for an additional waveguide film deposition. The substrate is preferably made of fused silica, a glass, or plastic material, such as cyclic-olefin copolymer (COC). For example, the GCW sensor 100 can have a cyclo-olefin substrate 112, which has an index $n_s=1.53$, a grating pitch $\Lambda=538$ nm, a grating thickness is $t_g=10$ nm, a waveguide index $n_f=2.01$, a waveguide thickness $t_f=110$ nm, and a superstrate index that is nominally the index of water (the solvent in which most experiments are performed, $n_c \gtrsim 1.33$). Of course, these particular values for the physical properties are only nominal values, since all material properties change with temperature and wavelength and other sensor designs may employ different materials.

The presence of biological or chemical analytes 102 on or near the sensing region alters the index of refraction at the surface 104 of the GCW sensor 100. Thus, to detect the biological analytes 102, the GCW sensor 100 is investigated with a light beam 126 emitted from the light source 122 and then a reflected light beam 128 received at the detection system 124 is analyzed to determine if there are any changes (~1 part per million) in the refractive index caused by the presence of the biological substance 102 in the sensing region 103 of the GCW sensor 100. In one embodiment, the top surface 104 may be coated with biochemical compounds (not shown) that only allow surface attachment of specific complementary biological substances 102 which enables an GCW sensor 100 to be created that is both highly sensitive and highly specific. In this way, the optical interrogation system 120 and GCW sensors 100 may be used to detect a wide variety of analytes 102. If the GCW sensors 100 are arranged in arrays they may be used to enable high throughput drug or chemical screening studies.

Furthermore, it should be appreciated that the interrogation instruments are not necessarily limited to working with reflected signal. An interrogation instrument can also work with waveguide coupled light (peak) or transmitted light (dip). Aspects of these light sources merely changes the location of the detection optics with a reader instrument without changing the principle attributes of the present invention, while providing possibly a means of avoiding spurious optical signals, such as unwanted substrate reflections, etc.

The sensitivity of the GCW sensor 100 may be best understood by analyzing the structure of the diffraction grating 108 and the waveguide 110. The physical operation of GCW devices can be understood as an interaction between a free-space light field and the environmentally-sensitive GCW waveguide modes. This interaction is made possible by the diffraction grating, designed to diffract light of specific wavelengths at specific angles to their incoming propagation vectors. As will be described more fully herein, the angular interrogation slope (AIS) or wavelength interrogation slope (WIS) are primary measures of sensor response, depending upon the particular parameters of experimental interrogation scheme. AIS and WIS, respectively, refer to the amount of sensor angle or wavelength shift that occurs in response to a unit change of refractive index at the sensor surface.

In the GCW device, a particular wavelength incident at a particular angle will diffract directly into the fundamental mode of the waveguide, and propagate for some (short) distance. The coupling between grating and waveguide preserves momentum, and detailed mathematics can be found in the literature; for brevity, we will simply mention that the difference in the real part of the x-propagation coefficient between the free-space and waveguide mode will equal the wavevector of the grating. The light beam 126 shone on the diffraction grating 108 can only be coupled into the waveguide 110 if its wave vector satisfies the following resonant condition as shown in Equation No. 1:

$$k_x' = k_x - \kappa \quad [1]$$

where $k_x'$ is the x-component of the incident wave vector, $k_x$ is the guided mode wave vector, and $\kappa$ is the grating vector. The grating vector $\kappa$ is defined as a vector having a direction perpendicular to the lines of the diffraction grating 108 and a magnitude given by $2\pi/\Lambda$ where $\Lambda$ is the grating period (pitch). This expression may also be written in terms of wavelength $\lambda$ and incident angle $\theta$ as shown in Equation No. 2:

$$\frac{2\pi n_{inc}}{\lambda} \sin\theta = \frac{2\pi n_{eff}}{\lambda} - \frac{2\pi}{\Lambda} \quad [2]$$

Where $\theta$ is the angle of incidence of the light beam 126, $n_{inc}$ is the index of refraction of the incident medium, $\lambda$ is the wavelength of the light 126, and $n_{eff}$ is the effective index of refraction of the waveguide 110. The effective index of the waveguide 110 is a weighted average of the indices of refraction that the optical waveguide mode field or fundamental mode "sees" as it propagates through the waveguide 110. The fundamental mode preferably has a spatial extent that is wider than the waveguide 110 itself, the extent depending on the refractive index of the substrate 112. In particular, the fundamental mode has an evanescent wave/tail that extends into the superstrate 103 (sensing region) which "sees" any surface changes created when the biological substance 102 approaches or comes in contact with the top surface 104 of the GCW sensor 100.

Figure 2:
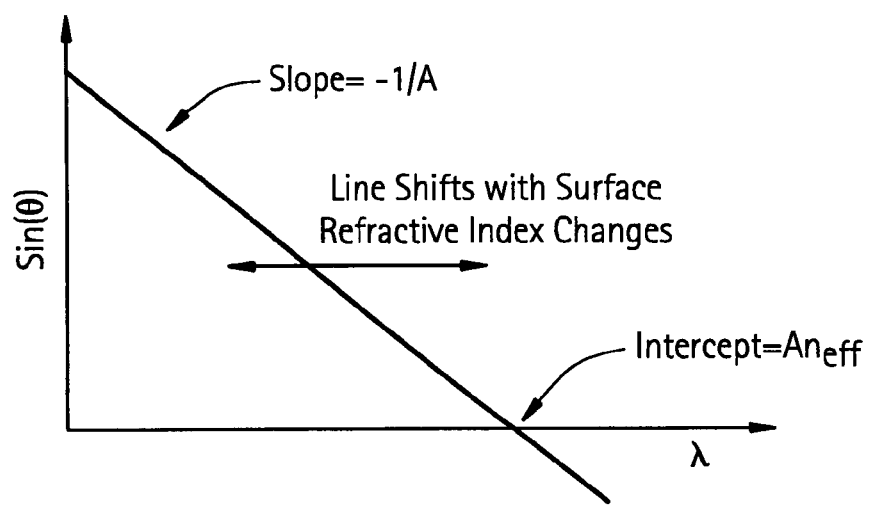
FIG. 2 is a graph that illustrates the relationship between the resonant angle and resonant wavelength of the GCW sensor shown in FIG. 1.

The previous expression shown in Equation No. 2 may be rewritten in the more convenient form shown in Equation No. 3:

$$\sin\theta = n_{eff} - \frac{\lambda}{\Lambda} \quad [3]$$

which is the equation of a line where $\sin\theta$ being the y axis, $\lambda$ being the x-axis, $\Delta n_{eff}$ the x-intercept, and $-1/\Lambda$ the slope. To obtain Equation No. 3, $n_{inc}$ has been set to 1 so that it could be removed from Equation No. 2. This approximation is used since air ($n \approx 1.0003$) is the most common incident medium. This relation is pictured in the graph shown in FIG. 2. When a biological substance 102 binds to the surface 104, the effective index of the waveguide 110 is altered which leads to the shifting the resonant wavelength or resonant angle of the GCW sensor 100. This shifting can be seen as a shift of the x-intercept in the line shown in FIG. 2.

In other words, $$\beta_g - \beta_x = \frac{2\pi}{\Lambda} \quad [4]$$

where $\beta_g$ is the waveguide propagation constant, $\beta_x$ is the free-space propagation constant parallel to the grating vector and waveguide mode constant $\beta_g$, and $\Lambda$ is the grating period. The same grating that couples this particular wavelength into the grating will also serve to couple this light back out of the waveguide, according to the same diffraction angle laws that governed the input coupling. The net result is the angular redirection of a narrow wavelength band of light incident on the GCW device. This narrowband response is often referred to as a Wood anomaly. The design of the device determines the input angle and wavelength for waveguide coupling, as well as the output angle. This type of functionality is analogous to directional optical filtration, with obvious applications wherever optical filters are needed.

GCW devices with an ability to tune the location, in both spectral wavelength and angle, of the above resonance with the index of refraction of the waveguide superstrate are useful in biosensors. As mentioned before, typically the evanescent tail of the propagating waveguide mode senses the superstrate index changes, thereby altering the guided mode's effective index. This changes the resonance condition of the GCW according to Equation No. 4, above, and the resonance thus shifts to a new wavelength or angle location.

Figure 3:
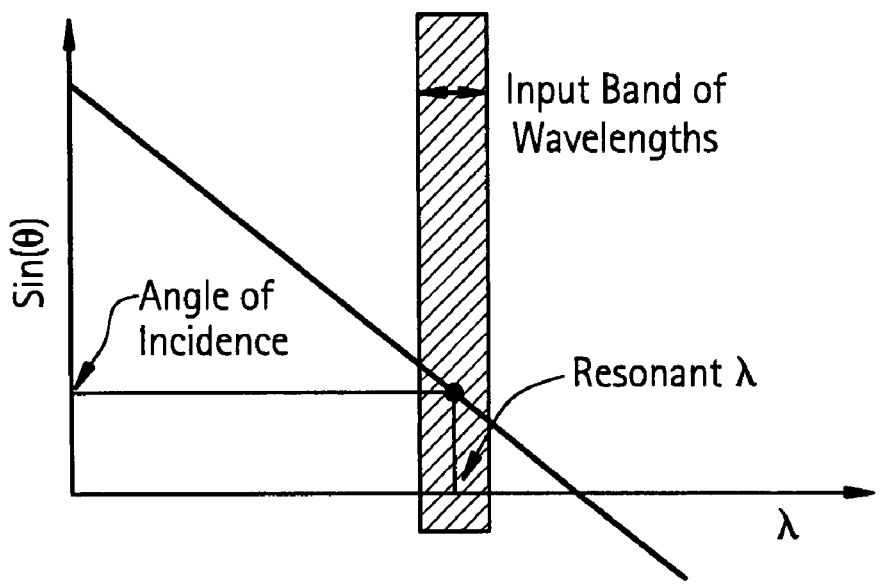
FIG. 3 is a graph used to help describe how a spectral interrogation approach can be used by the optical interrogation system to determine the resonant wavelength of the GCW sensor shown in FIG. 1.
Figure 4:
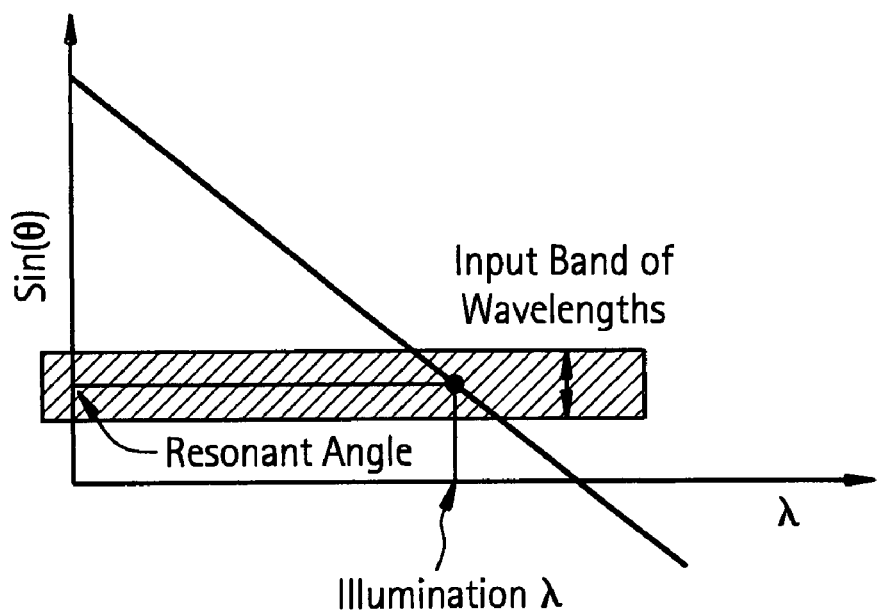
FIG. 4 is a graph used to help describe how an angular interrogation approach can be used by the optical interrogation system to determine the resonant angle of the GCW sensor shown in FIG. 1.

Referring to FIG. 1, the resonant condition (e.g., resonant wavelength or resonant angle) of such a GCW 100 may be interrogated to determine refractive index changes by observing the reflected light 128 from the GCW 100. There are two different modes of operation for monitoring refractive index changes—spectral interrogation or angular interrogation. In spectral interrogation, a nominally collimated, broadband beam of light 126 is sent into the GCW 100 and the reflected light 128 is collected and monitored with a spectrometer 124 (for example). By observing the spectral location of the resonant wavelength (peak), one can monitor binding or refractive index changes on or near the surface 104 of the GCW 100. The spectral interrogation concept is graphically represented in the graph shown in FIG. 3. Conversely, in angular interrogation, a nominally single wavelength of light 126 is focused to create a range of illumination angles and directed into the GCW 100. The reflected light 128 is monitored with a CCD camera or other optical detector 124. By monitoring the position of the resonant angle reflected by the GCW 100, one can monitor binding or refractive index changes on or near the surface 104 of the GCW 100. The angular interrogation concept is graphically represented in the graph shown in FIG. 4.

Figure 5:
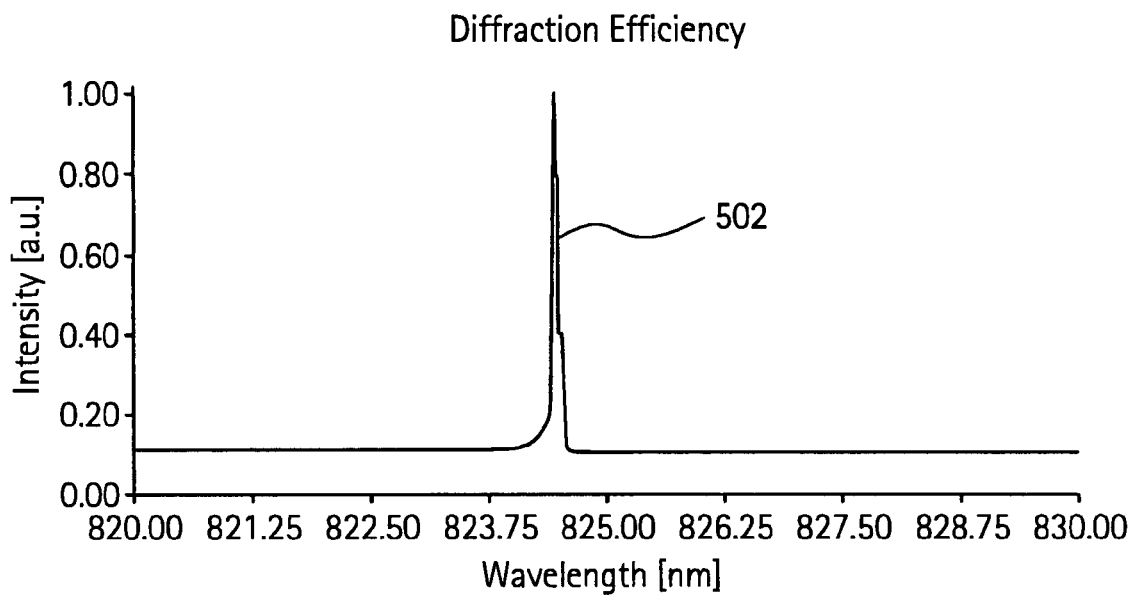
FIG. 5 is a graph that illustrates the resonant wavelength (reflection anomaly) of an exemplary GCW sensor having a substrate made from cyclo-olefin and a waveguide film made from $Ta_2O_5$.

In order to maintain simplicity and efficiency of operation, the devices employed for biosensing are usually designed such that only the zeroth diffracted orders of the grating propagate in free space, while what would be the ±1 orders couple to the fundamental mode of the waveguide. The higher diffraction orders are avoided by designing a sub-wavelength grating (i.e., grating pitch is smaller than the desired operating wavelength). The coupling efficiency is large since multiple orders do not remove power from the system. Moreover, since only the zeroth reflected and transmitted beams exist in free space, the GCW can thereby produce nearly total reflection or transmission of the desired (anomalous) wavelength. FIG. 5 shows a GSOLVER (rigorous coupled-wave analysis, or RCWA code) analysis of the structure of the device illustrated in FIG. 1, when the input light angle is about 3°. The reflected beam (at 3° from the normal) occurs in the vicinity of about 824 nm for incident TE light and at a cover index of 1.33 (water).

As mentioned above, GCW sensors 100 are used in biosensing applications because they enable one to determine the location of the resonance angle/wavelength 502 which enables one to calculate the refractive index of the superstrate 103 and then determine whether or not a biological substance 102 is located on the GCW sensor 100. This is all possible because the evanescent tail of the propagating fundamental mode in the waveguide 110 senses index changes in the superstrate 103 caused by the presence of the biological substance 102. The index change in the superstrate 103 changes the resonance condition of the GCW 100 according equation no. 1 and then the resonance 502 shifts to a new wavelength or angle location. The location of the shifted resonance indicates the current index of the superstrate 103 which indicates whether or not the biological substance 102 is in the superstrate 103 of the GCW 100. It has been shown that the resonance 502 can shift hundreds of nanometers for a unit change in the refractive index of the superstrate 103 (see FIG. 2). The relationship between angle and wavelength is displayed in the graph of accompanying FIG. 6, for a BIOS-1-GCW sensor 100. The different curves show behavior for both TE and TM polarizations for two different cover indices.

Figure 6:
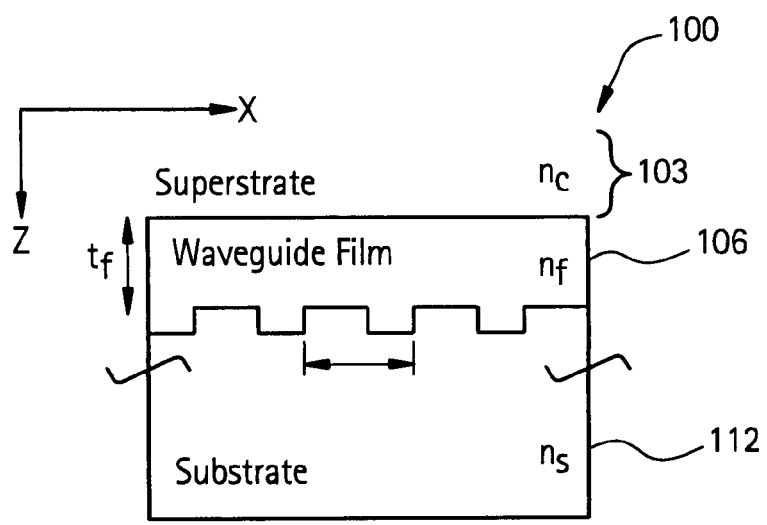
FIG. 6 is a graph illustrating the relationship between the resonant angle and wavelength of an exemplary GCW sensor that has two different cover indices.
Figure 7A:
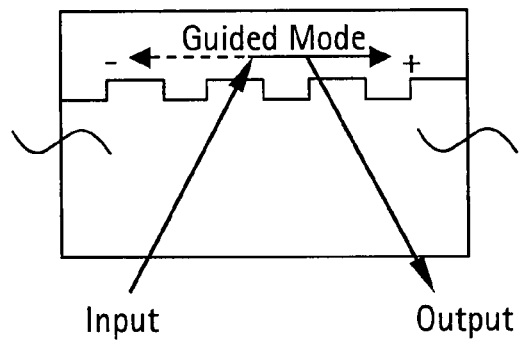
FIG. 7A shows the convention for forward (+) and reverse (−) propagation given certain input and output directions.

The curves displayed in FIG. 6 were calculated using rigorous coupled-wave analysis (RCWA), and present the unique solution in wavelength and angle space for a given input beam orientation. At any given wavelength and input beam orientation, the optical energy will couple to only one propagation direction in the waveguide, depicted by the solid line waveguide mode in FIG. 7A. Positive angles in FIG. 6 represent this solid (+) mode of FIG. 7A: an incident beam whose propagation vector x-component is in the same direction as the waveguide mode, equivalent to $\beta_g$ and $\beta_x$ having the same sign in Equation No. 4. Likewise, negative angles in FIG. 6 represent an incident beam propagation vector x-component oriented in the opposite direction relative to the waveguide mode; this is depicted in FIG. 7A by the dashed (—) waveguide mode, and is equivalent to $\beta_g$ and $\beta_x$ having opposite signs in Equation No 4. While both directions are displayed in FIG. 7A, it should be emphasized that these oppositely-directed waveguide modes do not necessarily exist simultaneously for the same input wavelength; FIG. 6 should again be consulted for the proper wavelengths given inverse angles.

The single solution angle/wavelength curves of FIG. 6 can be reflected about the zero-angle axis to produce the mirror solutions. One may rewrite Equation No. 4 in terms of the incident (or reflected) angle θ and the effective index of the waveguide $n_{eff}$:

$$\sin\theta = n_{eff} - \frac{\lambda}{\Lambda} \qquad [5]$$

The "double" resonance condition for the grating sensor arises from the fact that there is a second resonance condition obtained by setting θ equal to −θ in the above equation. As will be described in detail later, this second resonance arises from the symmetry of the sensor:

$$\sin\theta = -n_{eff} + \frac{\lambda}{\Lambda} \qquad [6]$$

Figure 7B:
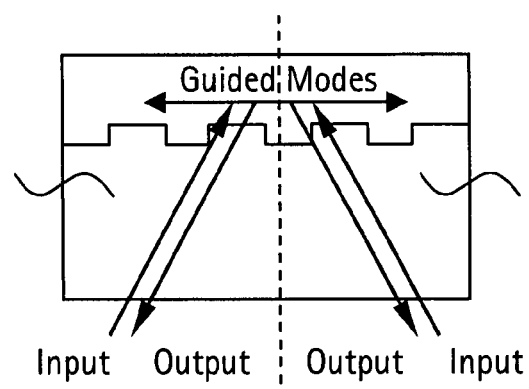
FIG. 7B shows the result of a mirror reflection of FIG. 7A about a vertical axis (normal incidence axis), showing the symmetry possible when considering input from both sides of the sensor.
Figure 7C:
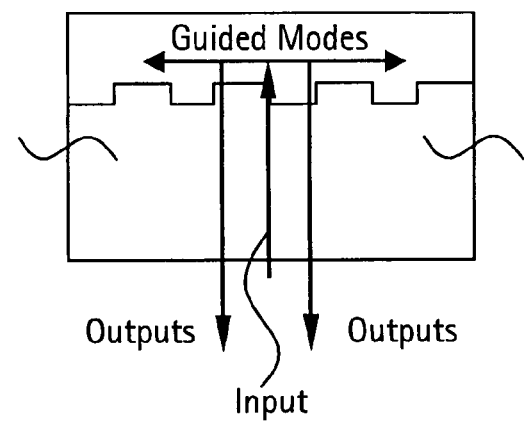
FIG. 7C shows the doubly degenerate case when the input/output beams strike the GCW sensor at normal incidence, simultaneously exciting oppositely directed propagating modes.

Since the sensor is symmetrical in the horizontal direction, the geometry of FIG. 7A can be reflected about a vertical line to produce its mirror image, resulting in duplicate positive-angle, waveguiding directions as shown in FIG. 7B. This situation is easily realized in the laboratory by launching a converging or diverging optical beam that contains enough angular spread to satisfy both the positive and negative conditions simultaneously, or by launching two separate input beams into the sensor device at the appropriate (mirror) angles. The limiting case of this geometry is the auto-symmetric normal-incidence launch depicted in FIG. 7C. In this case, a single input beam is able to excite both waveguiding directions simultaneously.

A double resonance concept can be applied for both angular and wavelength-based interrogation methods. On one hand, if one assumes that the resonant coupling angle is the observable, and that wavelength is fixed, then one can subtract Equations Nos. 5 and 6 to obtain:

$$\theta^{difference} \approx \sin\theta^+ - \sin\theta^- = 2\left(n_{eff} - \frac{\lambda}{\Lambda}\right) \quad [7]$$

Figure 8:
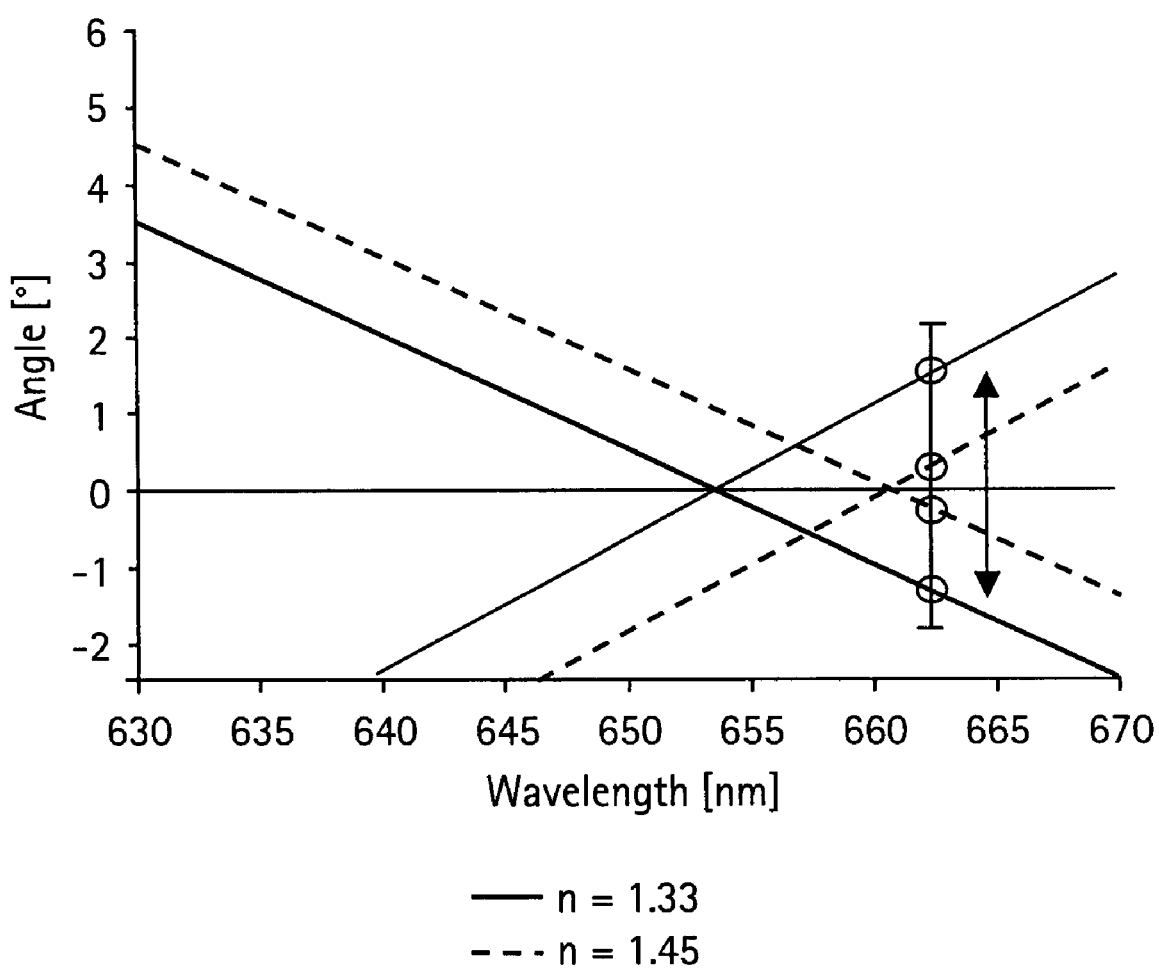
FIG. 8 shows the mirror symmetry produced by reflecting the theoretical curves of FIG. 6 about the zero-degree (normal incidence) axis, again explicitly showing the resonance conditions possible when striking the GCW sensor from both positive and negative angles. Superimposed on this figure is a vertical line segment representing the single-wavelength, multi-angular content of a typical angular interrogation system (such as in FIG. 9A). The circles show intersections of this optical beam with the resonance curves, indicating the resonance locations for the system. As the GCW superstrate index changes (due to a biological reaction, for example), the resonances move from the dashed curves to the solid curves, or vice versa. This demonstrates how the apparent sensor response doubles compared to a single resonance system when the difference between resonance locations is considered under this scheme.

Equation No. 7 represents the angular "difference" observable that may be used as an effective index measure in the angular interrogation system. As was mentioned, the signal is the difference between the two resonant angles. As the cover index changes, the two peaks will either move together or apart (the wavelength does not change in the angular interrogation scheme). By observing both the positive and negative resonances, one doubles the amount of signal available, and if the noise in each measurement is uncorrelated, the improvement in signal to noise ratio is about a factor of $\sqrt{2} \approx 1.414213$. For example, FIG. 8 illustrates the phenomenon by an angular interrogation scheme for two different superstrate indices of refraction.

Figure 9A:
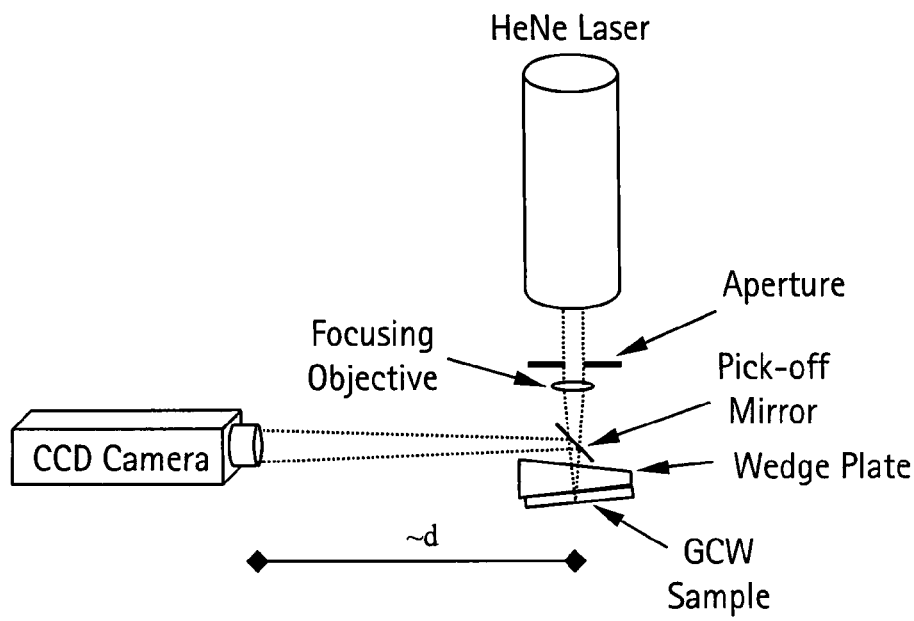
FIG. 9A is a schematic of an angular interrogation optical system, where a single-wavelength laser beam is focused to generate a collection of angles on the GCW sample, and the reflected beam is analyzed by a CCD camera.
Figure 9B:
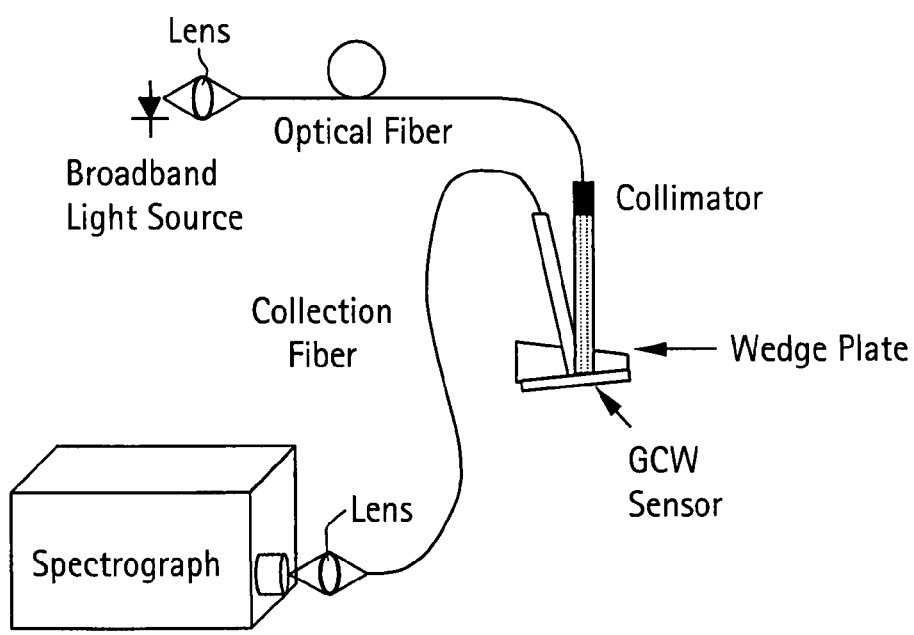
FIG. 9B is a schematic of a spectral interrogation system, where a multi-wavelength beam impinges on the GCW sample from a single angle, and the reflected beam is analyzed by a spectrograph.

In a system for an angular interrogation device, such as depicted in FIG. 9A, a collection of angles is incident upon the sensor at a single wavelength. This corresponds to the finite-length vertical lines $\alpha$ and $\beta$ in FIG. 8, where the length of the line represents the angular extent of the incoming beam. These lines graphically illustrate the basic core of the present double resonance concept. That is, for a given input wavelength, two resonances exist simultaneously due to the possibility of two propagation directions in the waveguide. One should ensure that the incoming optical beam contains enough angular or wavelength spectrum to excite both propagation directions, either simultaneously or in sequence. For instance, the dashed line (n=1.45) of FIG. 8 represents data which suggest that a 662 nm input beam focused to contain at least ±2° will excite simultaneously both resonances for a given superstrate index.

According to desired operations of the sensor, one should focus attention on how the resonance locations change with index changes. This is demonstrated by observing the movement of the resonances when shifting from the green curves to the solid line (n=1.33 superstrate index). The arrows in FIG. 8 indicate that the resonances move in opposite directions relative to each other when the superstrate index is varied. Recalling that the sensor was designed to target a specific AIS (angular interrogation slope—the angular shift of the resonance for given superstrate refractive index change) for any single resonance, having two resonances move equal distances in opposite directions implies a doubling of the device sensitivity as per Equation [7], thus generating an improvement in the signal-to-noise of about $\sqrt{2}$ when each peak suffers from uncorrelated (Gaussian) noise.

Figure 10:
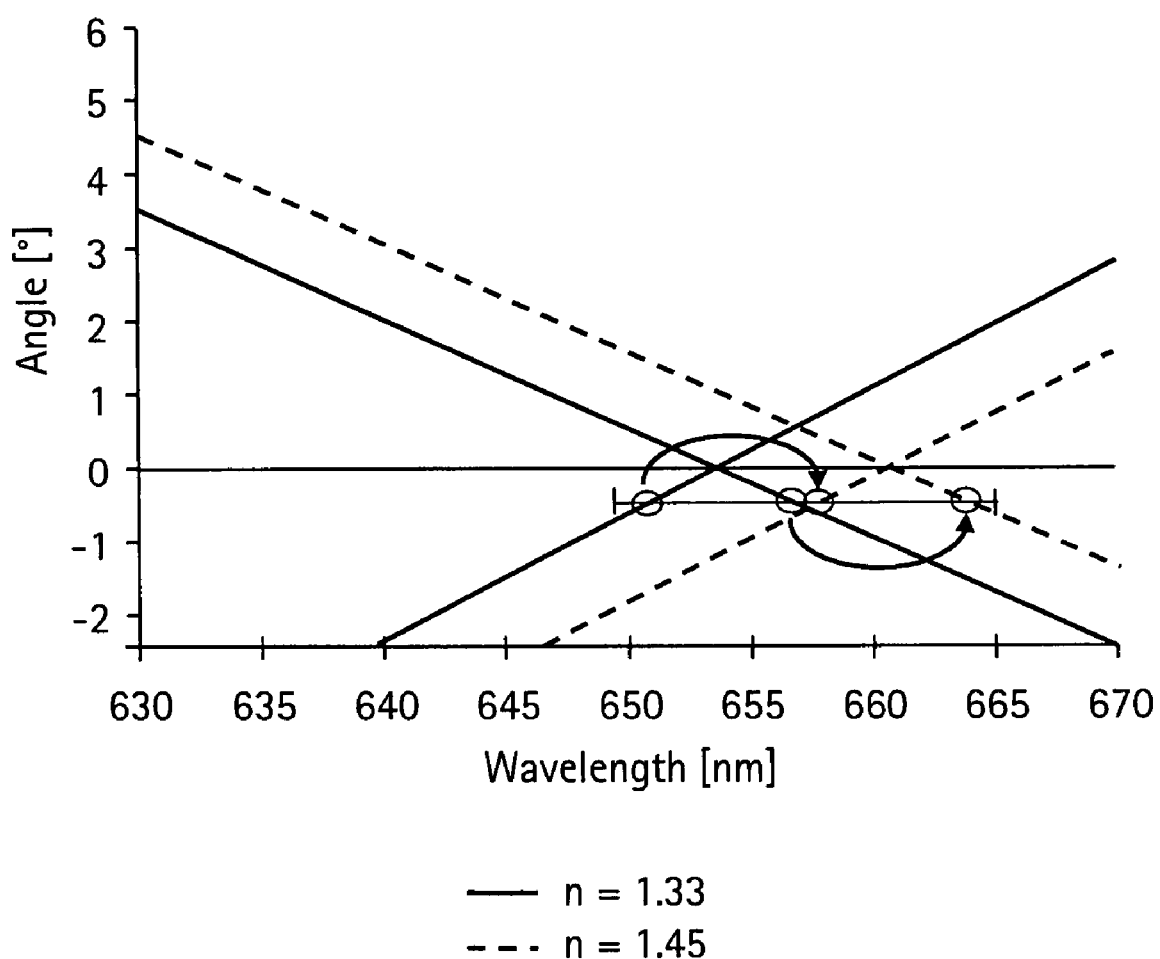
FIG. 10 shows the mirror symmetry produced by reflecting the theoretical curves of FIG. 6 about the zero-degree (normal incidence) axis, again explicitly showing the resonance conditions possible when striking the GCW sensor from both positive and negative angles. Superimposed on this figure is a horizontal line segment representing the multi-wavelength, single-angle content of a typical spectral interrogation system (such as in FIG. 7B). The circles show intersections of this optical beam with the resonance curves, indicating the resonance locations for the system. As the GCW superstrate index changes (due to a biological reaction, for example), the resonances move from the solid curves to the dashed curves, or vice versa. This demonstrates how averaging could be used to reduce the noise typically encountered in a single resonance system, since two resonances move together under this scheme.

In wavelength-based interrogation, the input beam is directed at a unique angle, but contains a band of different wavelengths. The analysis of this scenario is depicted in FIG. 10, where a horizontal line corresponds to single-angle, multi-wavelength interrogation. As FIG. 10 illustrates, under wavelength or spectral interrogation the double resonances shift in parallel with each other. In other words, the foci of the resonances move in the same direction as each other.

In order to analyze this spectral system, one can again subtract Equations Nos. 5 and 6 (where the angle is now constant and the wavelength varies) to obtain:

$$\lambda^{mean} \approx \frac{\lambda^+ + \lambda^-}{2} = \Lambda n_{eff} \quad [8]$$

The meaningful signal for wavelength interrogation is the mean (average) wavelength of the two spectral resonances. As the cover index changes, the mean value of the two spectral peaks will either shift to higher or lower wavelength. For instance, with regard to a general Gaussian-distributed noise source, the improvement in signal-to-noise averaging occurs as the square root of n ($\sqrt{n}$), where n is the number of averages. This calculation implies that, for wavelength interrogation, just as in the case of the angular measurement, one can improve the signal-to-noise-ratio by a factor of about $\sqrt{2}$ for uncorrelated noise.

B. Robustness against Environmental Noise

We note that the use of the double resonance enables either the angular or spectral-wavelength sensors to reject certain types of noise. Most prominent among external noise sources is the absolute angular position of the GCW sensor in the detection instrument. In particular, given a fixed optical beam, how will the detected resonance signal vary when the GCW sensor is tilted? The angular interrogation system will be insensitive to this noise provided the angular misalignment does not exceed the total angular content of the input beam, since both resonances move the same direction when the sensor is tipped, and the difference in angular peak locations is therefore constant. This is demonstrated schematically in FIG. 11 are affected equally, thus canceling out the each other.

Analogously, for the spectral sensor, the observation of the mean of the double resonance signal will allow one to reject any angular jitter in the apparatus, since this type of jitter will cause the peaks to move together or apart, but will not affect their mean value (see FIG. 10). This angular jitter is an example of common mode noise that the double resonance design will robustly reject, possibly improving the observed signal to noise in the system by much more than square root of (2), depending on the magnitude of the various noise sources.

According to these characteristics of the invention, signals from different propagation directions can be employed to mitigate the system's sensitivity to extraneous environmental perturbations. In other words, the difference present in resonant peak locations and/or the average pf resonant peak locations are made less dependent on the vagaries of substrate placement and less sensitive to angular position of the sensor, while heightening the ability of the detection instrument to sense the true signals. Similarly, the differences present in resonant peak locations and/or the average of resonant peak locations are insensitive to wavelength noise.

C. Deviations from Simple Theory

The analysis of the above section, particular the results in Equations [7] and [8], are somewhat simplified for ease of understanding. A more detailed analysis starting with equations [5] and [6] can indicate what other factors must be considered for robust, accurate use of the double resonance technique.

For the angular measurement system, a single wavelength is used, and the angles used to couple into the waveguide are equal and opposite ($\theta_1 = -\theta_2$), resulting in equal waveguide effective indices. Equations [5] and [6] therefore become:

$$\sin\theta_1 = n_{eff} - \frac{\lambda}{\Lambda}$$ [9]

$$\sin\theta_2 = -n_{eff} + \frac{\lambda}{\Lambda}$$

The difference of these two equations is therefore $$\theta_1 - \theta_2 = \sin^{-1}\left(n_{eff} - \frac{\lambda}{\Lambda}\right) - \sin^{-1}\left(-n_{eff} + \frac{\lambda}{\Lambda}\right)$$ [10]

$$\Rightarrow \text{observable} = 2\sin^{-1}\left(n_{eff} - \frac{\lambda}{\Lambda}\right)$$

meaning that one must first take the sin of ½ of the observable parameter to deduce true changes in superstrate index (the wavelength and grating pitch do not change during the course of a measurement). This still displays the doubled response characteristic of the simplified analysis and reduces to the simplified result of Equation [7] in the case of small angles.

In the case of the wavelength interrogation system, the input/output angles are fixed, while the wavelength of each separate resonance is different. Likewise, due to the different wavelengths, the effective indices of the separate waveguide modes are different. Reflecting this in equations [5] and [6], $$\sin\theta = n_{eff,1} - \frac{\lambda_1}{\Lambda}$$ [11]

$$\sin\theta = -n_{eff,2} + \frac{\lambda_2}{\Lambda}$$

Next, we define the observable parameter of interest, the average wavelength:

$$\lambda_a = \frac{\lambda_1 + \lambda_2}{2}$$ [12]

It is the derivative of this quantity with respect to angle that the double resonance technique hopes to minimize and thereby make the sensor more tolerant to angular misalignments.

Next, since the two resonance wavelengths change when the angle changes (according to Equation [11]), the dispersion in the waveguide system will cause the effective indices to likewise change. Since the average wavelength is expected to vary slowly, we expand the effective indices around this average wavelength, $$n_{eff} = n_a + \Delta\lambda \frac{dn_{eff}}{d\lambda}\bigg|_{\lambda_a} + \frac{\Delta\lambda^2}{2} \frac{d^2 n_{eff}}{d\lambda^2}\bigg|_{\lambda_a} + \ldots$$ [13]

$$= n_a + \Delta\lambda D_a + \frac{\Delta\lambda^2}{2} D'_a + \ldots$$

where $D_a$ is the effective index dispersion evaluated at $\lambda=\lambda_a$, and the term $\Delta\lambda$ has opposite sign for the two resonances:

$$\Delta\lambda_1 = \lambda_1 - \lambda_{avg}$$

$$\Delta\lambda_2 = \lambda_{avg} - \lambda_2 = -\Delta\lambda_1$$ [14]

We can now substitute the effective index expansion [13] (to second order) into each resonance condition [11], and use these in the average wavelength expression [12]

$$\lambda_a = \frac{\Lambda}{2}\left(n_a + \Delta\lambda_1 D_a + \frac{\Delta\lambda_1^2}{2} D'_a - \sin\theta + n_a - \Delta\lambda_1 D_a + \frac{\Delta\lambda_1^2}{2} D'_a + \sin\theta\right)$$ [15]

$$= \Lambda\left(n_a + \frac{\Delta\lambda_1^2}{2} D'_a\right)$$

Taking the derivative of the above expression with respect to angle, we obtain the parameter of interest:

$$\frac{d\lambda_a}{d\theta} = \Lambda\Delta\lambda_1 D'_a\left(\frac{d\lambda_1}{d\theta} - \frac{d\lambda_a}{d\theta}\right)$$ [16]

In order to evaluate this expression, we must evaluate the individual resonance $\lambda_1$ derivative, $$\frac{d\lambda_1}{d\theta} = \Lambda\left(\frac{dn_{eff,1}}{d\theta} - \cos\theta\right)$$ [17]

$$= \Lambda\left(\frac{d}{d\theta}\left[n_a + \Delta\lambda_1 D_a + \frac{\Delta\lambda_1^2}{2} D'_a\right] - \cos\theta\right)$$

$$= \Lambda\left(D_a\left(\frac{d\lambda_1}{d\theta} - \frac{d\lambda_a}{d\theta}\right) + \Delta\lambda_1 D'_a\left(\frac{d\lambda_1}{d\theta} - \frac{d\lambda_a}{d\theta}\right) - \cos\theta\right)$$

Collecting terms on the left-hand side, we can evaluate this derivative:

$$\frac{d\lambda_1}{d\theta}\left[\frac{1}{\Lambda} - D_a - \Delta\lambda_1 D'_a\right] = \frac{-d\lambda_a}{d\theta}[D_a + \Delta\lambda_1 D'_a] - \cos\theta$$ [18]

$$\Rightarrow \frac{d\lambda_1}{d\theta} = \frac{\cos\theta + \frac{d\lambda_a}{d\theta}(D_a + \Delta\lambda_1 D'_a)}{D_a + \Delta\lambda_1 D'_a - \frac{1}{\Lambda}}$$

The derivative of the resonance average is therefore $$\frac{d\lambda_a}{d\theta} = \Lambda\Delta\lambda_1 D'_a\left(\frac{\cos\theta + \frac{d\lambda_a}{d\theta}(D_a + \Delta\lambda_1 D'_a)}{D_a + \Delta\lambda_1 D'_a - \frac{1}{\Lambda}} - \frac{d\lambda_a}{d\theta}\right)$$ [19]

$$= \Lambda\Delta\lambda_1 D'_a\left(\frac{\cos\theta}{D_a + \Delta\lambda_1 D'_a - \frac{1}{\Lambda}} - \right.$$

$$\frac{d\lambda_a}{d\theta}\left(\frac{D_a + \Delta\lambda_1 D'_a}{D_a + \Delta\lambda_1 D'_a - \frac{1}{\Lambda}} - 1\right)\right)$$

$$= \Lambda\Delta\lambda_1 D'_a\left(\frac{\cos\theta}{D_a + \Delta\lambda_1 D'_a - \frac{1}{\Lambda}} - \frac{d\lambda_a}{d\theta}\left(\frac{\frac{1}{\Lambda}}{D_a + \Delta\lambda_1 D'_a - \frac{1}{\Lambda}}\right)\right)$$

Now we can again arrange terms on the left-hand side to solve for the derivative, $$\frac{d\lambda_a}{d\theta}\left(\frac{1}{\Lambda\Delta\lambda_1 D'_a} - \frac{\frac{1}{\Lambda}}{D_a + \Delta\lambda_1 D'_a - \frac{1}{\Lambda}}\right) = \frac{\cos\theta}{D_a + \Delta\lambda_1 D'_a - \frac{1}{\Lambda}} \quad [20]$$

$$\Rightarrow \frac{d\lambda_a}{d\theta} = \frac{\cos\theta}{\dfrac{D_a + \Delta\lambda_1 D'_a - \dfrac{1}{\Lambda}}{\Lambda\Delta\lambda_1 D'_a} - \dfrac{1}{\Lambda}}$$

$$= \frac{\cos\theta}{\dfrac{D_a - \dfrac{1}{\Lambda}}{\Lambda\Delta\lambda_1 D'_a}}$$

$$= \frac{\Lambda\Delta\lambda_1 D'_a \cos\theta}{D_a - \dfrac{1}{\Lambda}}$$

Hence, we have the average resonance drift with respect to angle expressed in terms of the average effective index dispersion and its derivatives, the grating pitch ($\Lambda$), and $\Delta\lambda_1$, the ½ difference in resonance wavelengths. Since $\Delta\lambda_1$ involves both $\lambda_1$ and $\lambda_a$, we need to re-express this quantity in terms of only average values that drift much more slowly with changes in angle, $$\Delta\lambda_1 = \lambda_1 - \lambda_a \quad [21]$$
$$= -(\lambda_2 - \lambda_a)$$
$$= \Lambda(n_{\mathit{eff}1} - \sin\theta) - \lambda_a$$
$$\cong \Lambda(n_a + \Delta\lambda_1 D_a - \sin\theta) - \lambda_a$$
$$\Rightarrow \Delta\lambda_1[1 - \Lambda D_a] = \Lambda(n_a - \sin\theta) - \lambda_a$$
$$\Rightarrow \Delta\lambda_1 = \frac{n_a - \sin\theta - \dfrac{\lambda_a}{\Lambda}}{\dfrac{1}{\Lambda} - D_a}$$

We now have an expression for $\Delta\lambda_1$ in terms only of average parameters that vary slowly. Substituting this value into the expression for the average wavelength drift [20], we arrive at the final expression for the drift:

$$\frac{d\lambda_a}{d\theta} = \frac{\cos\theta \Lambda D'_a \left(\dfrac{n_a - \sin\theta - \dfrac{\lambda_a}{\Lambda}}{\dfrac{1}{\Lambda} - D_a}\right)}{D_a - \dfrac{1}{\Lambda}} \quad [22]$$

$$= \frac{\cos\theta \Lambda D'_a \left(\sin\theta + \dfrac{\lambda_a}{\Lambda} - n_a\right)}{\left(D_a - \dfrac{1}{\Lambda}\right)^2}$$

Equation [22] shows that, in order for a system designer to use the double resonance technique in the spectral interrogation system embodiment, they may need to consider and compensate for the dispersion of the waveguide. In fact, depending upon the system, one may even need to consider higher-order terms in the Taylor series used in Equation [13].

In order to gain some understanding of this correction in the spectral interrogation approach, one can evaluate the value of the average wavelength error [22] using a model sensor:

| $n_{sub}$ | $n_{wg}$ | $t_{wg}$ [nm] | $\Lambda$ [nm] | $t_g$ [nm] | $\theta$ [°] |
|---|---|---|---|---|---|
| 1.527 | 2.07 | 181 | 500 | 50 | 1.9 | where $n_{sub}$ is the substrate index, $n_{wg}$ is the waveguide index, $t_{wg}$ is the waveguide thickness, $\Lambda$ is the grating pitch, $t_g$ is the grating thickness, and $\theta$ is the nominal angle the input light beam makes with the GCW sensor.

Figure 13:
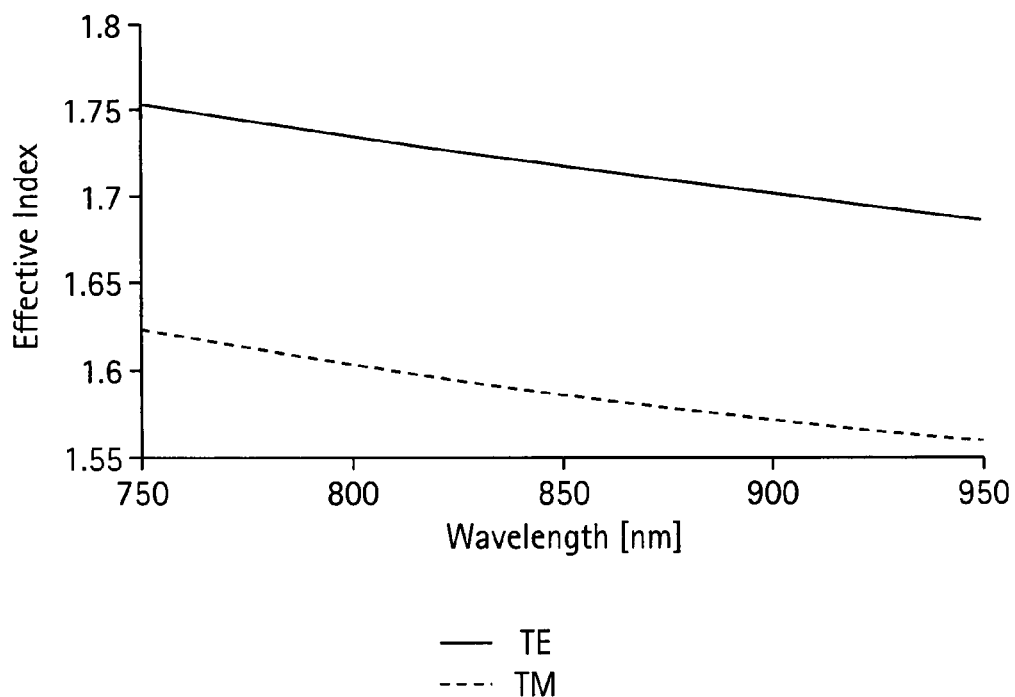
FIG. 13 shows the $n_{eff}$ vs. $\lambda$ curve for the experimental GCW structure used in the example calculation of the dispersion correction factor necessary to correctly insulate the FIG. 12 GCW sensor from angular misalignments.
Figure 14:
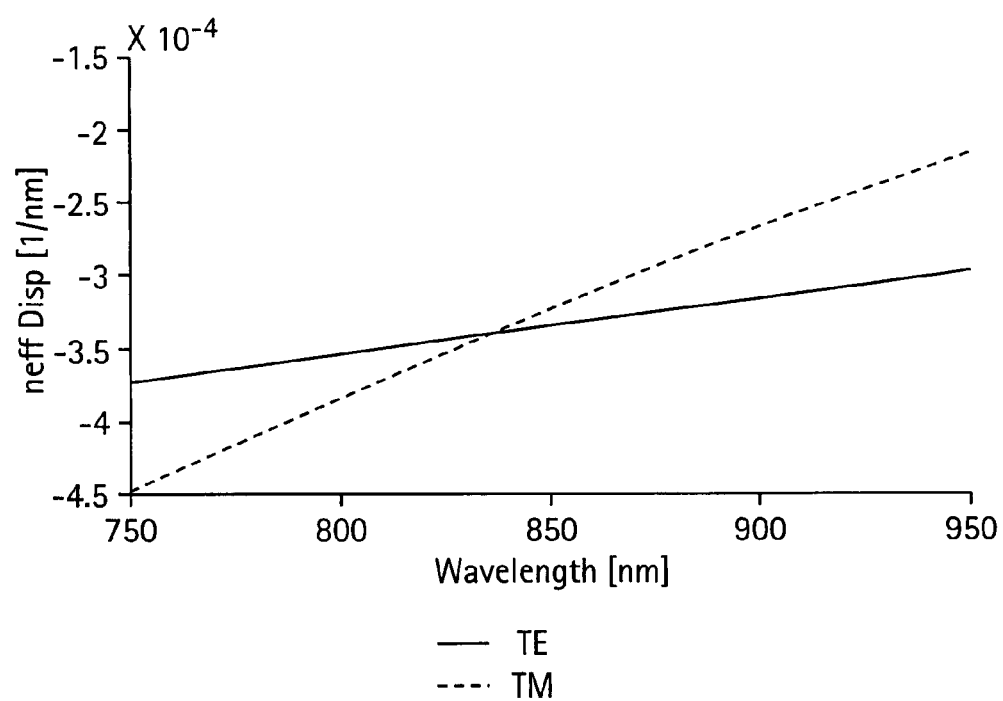
FIG. 14 shows effective index dispersion ($dn_{eff}/d\lambda$) vs. wavelength used in the example calculation of the dispersion correction factor necessary to correctly insulate the FIG. 12 GCW sensor from angular misalignments.
Figure 15:
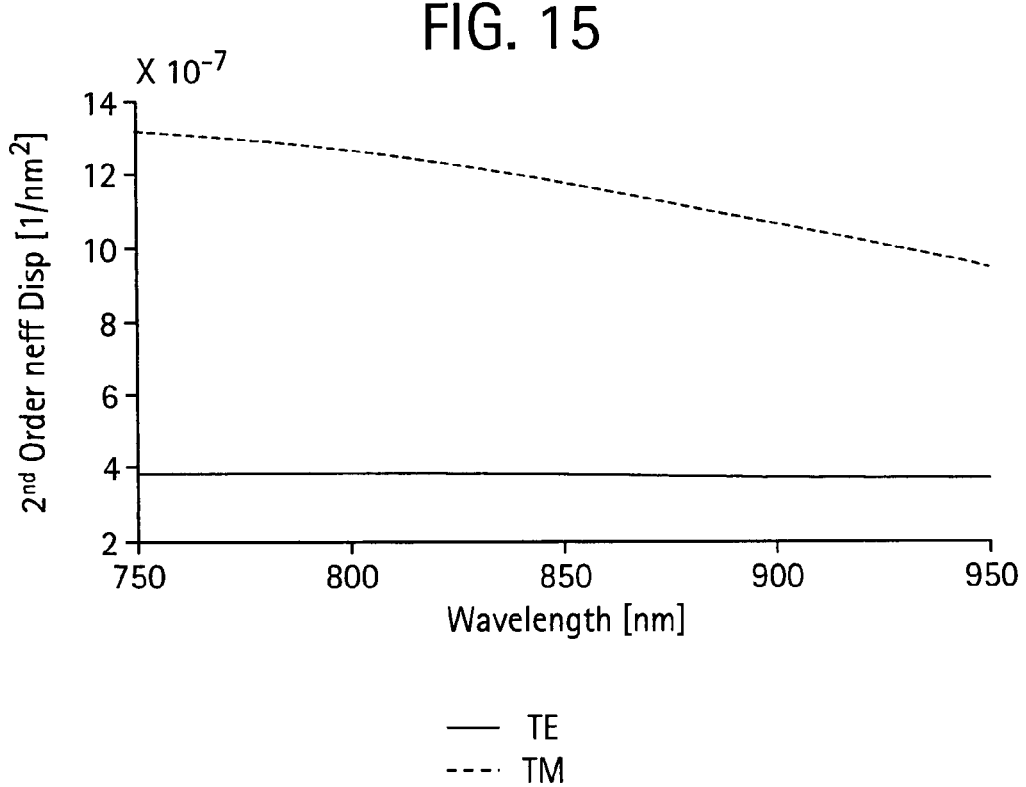
FIG. 15 is a graph of a second order effective index dispersion ($d^2 n_{eff}/d\lambda^2$) vs. wavelength used in the example calculation of the dispersion correction factor necessary to correctly insulate the FIG. 12 GCW sensor from angular misalignments.

This information is first used to calculate the modes of the structure, seen in FIG. 12. These are the modes as calculated at an operating wavelength of 830 nm. In the case of a double resonance, we will have two resonances from opposite propagation directions with different wavelengths. For the device of this example calculation with the input angle above, the resonances are equally spaced about an average wavelength value of ~801 nm (TM) and ~857 nm (TE) (this value depends upon the GCW design as well as the choice of input angle, etc.). We therefore need to know the effective index values for the modes at these average wavelengths in order to evaluate [10]. In addition, we need to know two orders of dispersion (derivatives of the effective index vs. wavelength curve) at these average values. In order to evaluate these derivatives, we have to calculate the effective index as a function of wavelength; this data is shown in FIG. 13, as calculated using the device specifications above. With the curve in FIG. 13 (and two orders of derivatives shown in FIGS. 14 and 15), the average wavelength drift can then be evaluated as a function of angle, shown ultimately in FIG. 16.

Figure 16:
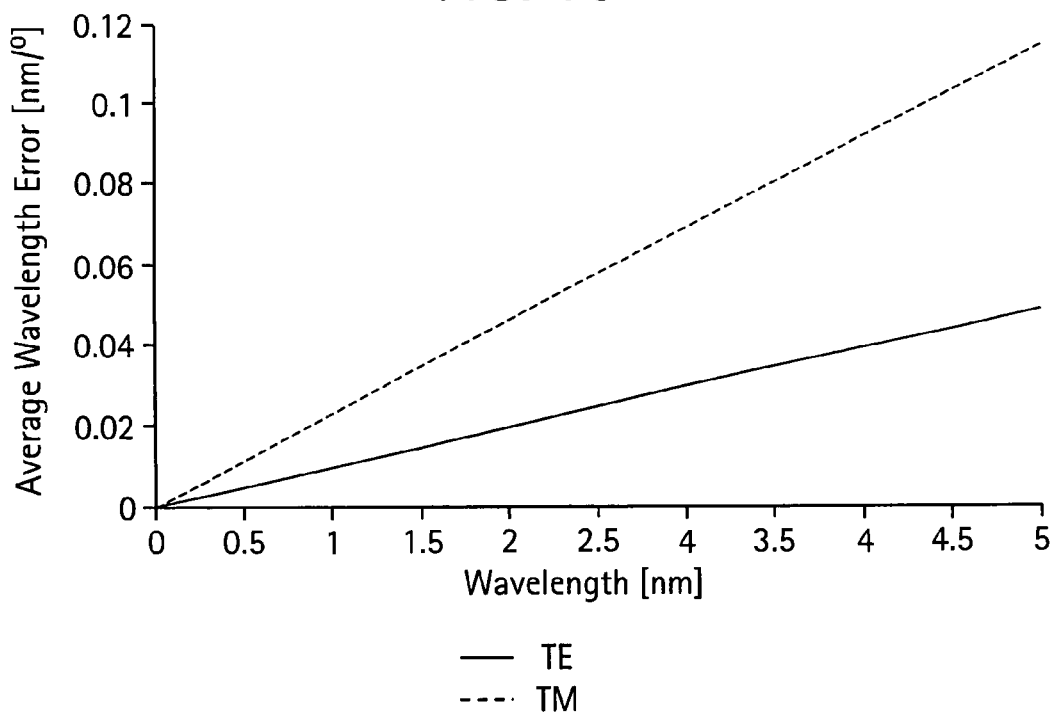
FIG. 16 shows the calculated residual wavelength error in the average resonance under the double resonance scheme using wavelength interrogation and the example sensor from FIG. 12.

FIG. 16 shows the existence of some residual average wavelength shift that must be accounted for in exact application of the double resonance scheme for angular insensitivity. At zero angle, the two wavelengths are degenerate, and the wavelength error is therefore zero. As the angle grows however, the two resonance wavelengths separate, and according to Equation [22] the effect of dispersion is to cause the average resonance wavelength to shift from the ideal center position. The TM correction is larger than the TE by about a factor of 2.3, mainly because the TM mode is closer to cutoff, and therefore has more wavelength dispersion. At an incidence angle of 1.9° for example, the TE wavelength error is 18.6 pm/°, whereas the TM wavelength error is 43.6 pm/°.

The following empirical section will demonstrate experimentally the observation of this average resonance error.

Section III—Empirical

A. Sensitivity Improvement

Figure 17:
FIG. 17 represents a typical single-resonance image. This resonance was found using a He—Ne laser at a wavelength of $\lambda$=633 nm, and required use of an incidence angle of ~5°, and the incoming cone of angles was ±0.7°.
Figure 18:
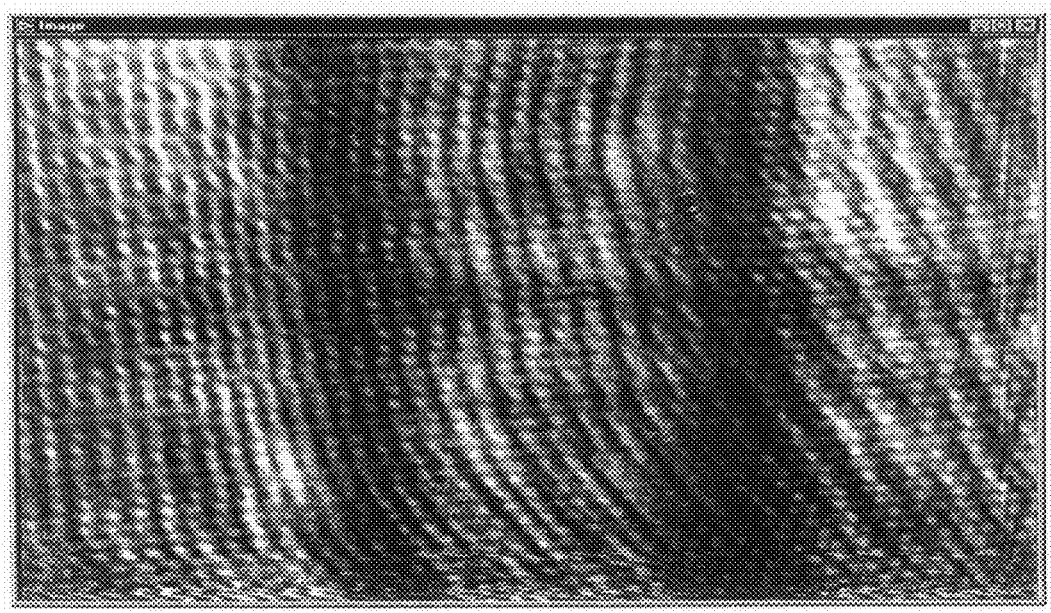
FIG. 18 represents a double-resonance image generated experimentally. Using a diode laser of $\lambda$=660 nm, one is able to view the double resonance at near normal incidence excitation of the waveguide.

In the laboratory, we have demonstrated the double resonance concept and other principles of the present invention using both a commercially-available BIOS-1 sensor and sensors fabricated by Corning Incorporated. FIG. 17 shows an image of a typical single GCW resonance under an angular interrogation scheme as bright vertical streak. This resonance was found using a HeNe laser where the wavelength ($\lambda$=633 nm) required the use of a relatively high angle of ~5°, and the incoming cone of angles was only ±0.7°. In order to view the double resonance, a $\lambda$=660 nm diode laser was employed, allowing near normal incidence excitation of the waveguide. FIG. 18 shows the experimental double resonance, in this case consisting of vertical shadows due to the presence of a large background reflection.

Aside from a simple demonstration that the double resonance is feasible, an experiment was performed with a series of sucrose solutions of varying refractive index applied to the sensor surface. This study was performed to address a concern that, while the symmetric peaks double the response to superstrate index changes, the noise of the system may likewise be doubled. If the peak detection is noise limited, and if both peaks contain uncorrelated Gaussian noise, then one would expect the peak separation noise variance to be two-times that of either peak separately. In such a situation, the reduction of the noise would be greater than single resonance operation by a factor of about $\sqrt{2}$ (since the standard deviation is the square root of the variance). If the noise in each peak is partially or completely correlated, the resulting signal-to-noise improvement can exceed a factor of $\sqrt{2}$. The noise associated with difference in signal can be less than the noise of either individual peak. A worst possible case is when the noise of each peak is anti-correlated, possibly negating the signal to noise benefit due to the double resonance technique, since the noise can double along with signal.

Figure 19:
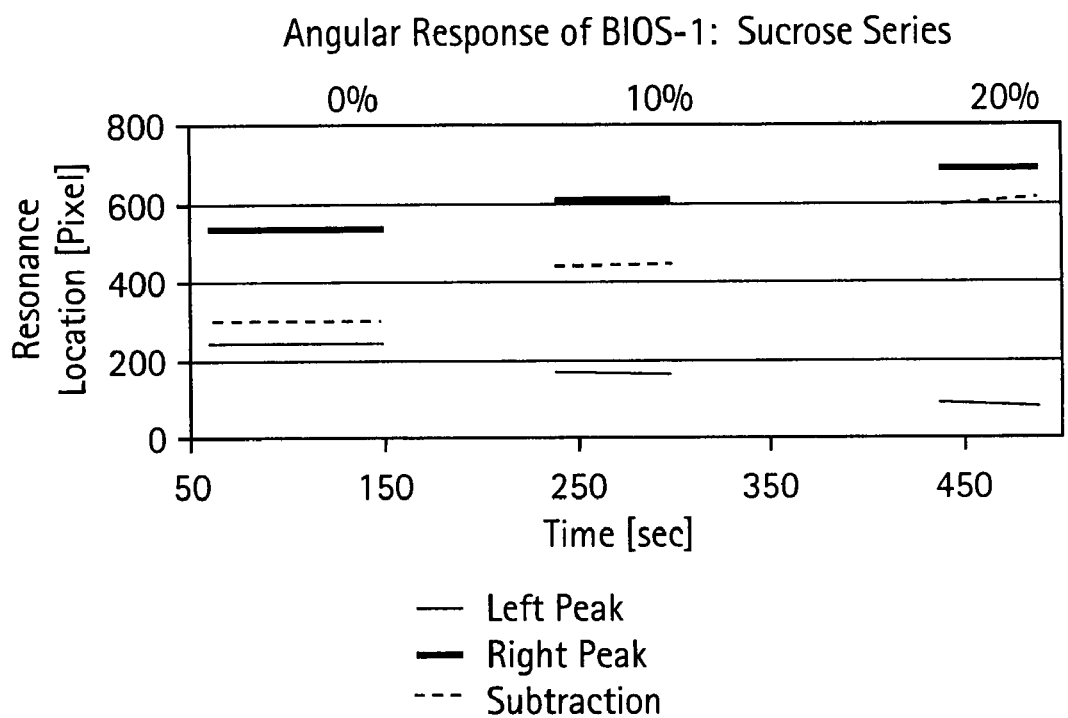
FIG. 19 represents the sucrose data collected using a double resonance, angular detection system. The image shows the result of exposing the GCW superstrate to a sucrose series at 0-10-20% concentration, where the gaps between each segment represents the time required to pipette the solutions onto the sensor. The location for the two separate peaks is shown, along with the peak difference.

The angular-based experiment involved monitoring the separation between the two resonances as a function of time. Since each resonance responds according to the device's AIS, the peak separation is the measure of the relative index of refraction of the superstrate. If the change in the peak separation per unit index change is called δp, and the standard deviation of the time-resolved peak location for a given constant cover index is used to quantify the system noise, then the minimum resolution of the systems can be experimentally calculated as:

$$\delta n = \frac{\text{Noise [Pixels]}}{\delta p[\text{Pixel}/RIU]} \quad [23]$$

where the peak location difference is measured in pixels on a CCD camera. The resonant wavelength or angle manifests itself as a narrow band of wavelength or angles on a screen through the CCD detection. FIG. 19 shows the result of a 0-10-20% sucrose series, where the gaps between each segment represents the time required to pipette the solutions onto the sensor. The location for the two separate peaks is shown, along with the peak difference. It is immediately apparent that the difference peak moves twice as far as either peak individually, confirming the index sensitivity hypothesis.

Figure 20:
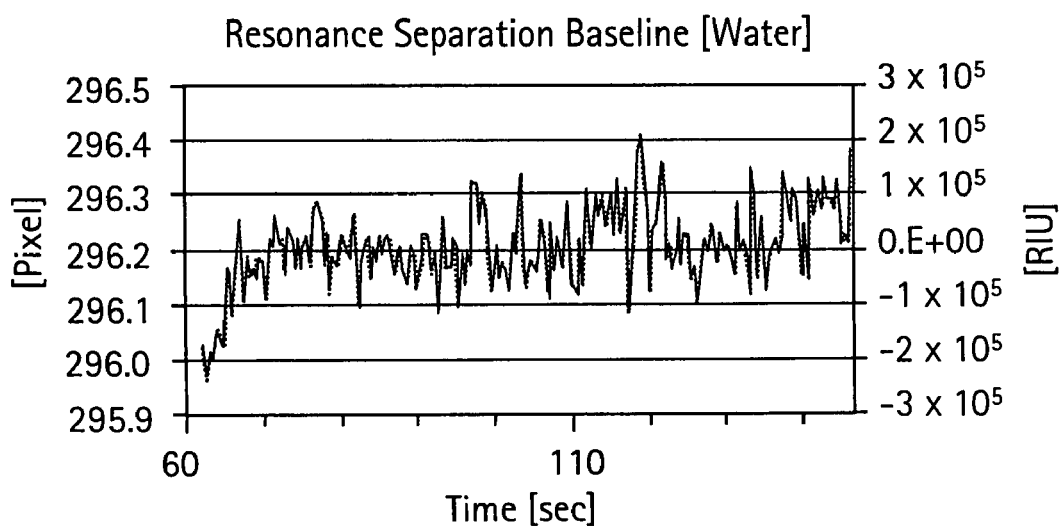
FIG. 20 represents the calculated baseline sensitivity over time, showing a detailed close-up of the sample with 0% concentration of sucrose (pure water) from FIG. 19, where the peak difference pixel units have been converted to index of refraction using the index data versus sucrose concentration of FIG. 19.

FIG. 20 shows a close-up view of the 0% sucrose (pure water) time history from FIG. 19, where the pixel units at the peak difference have been converted into index of refraction units using the index data versus sucrose concentration of FIG. 19. FIG. 20 shows that the baseline sensitivity is quite good, and the standard deviation of the data yields a detection limit of about $7\times10^{-6}$ refractive index unit (RIU). To quantify the impact of the peak difference operation on the noise of the system, the standard deviation (σ) of the two peaks separately were also calculated. This permits one to compare the variances of each data set. If the noise on each peak reflects uncorrelated Gaussian noise, then the variances should be additive as a result of the difference operation. If the difference variance, however, is less than the sum of the variances of each peak, then much of the noise would be correlated (common-mode) noise, and the differencing operation would significantly improve the noise of the system. Table 1 presents the data about variance for both peaks and their difference in the sucrose series.

TABLE 1

| Variance of Peaks | | |
|---|---|---|
| Left | Right | Difference |
| $6.28 \times 10^{-3}$ | $1.43 \times 10^{-2}$ | $4.95 \times 10^{-3}$ |

This data clearly shows that much of the noise from each peak was common-mode, since the difference variance is in fact less than either peak individually. This phenomenon permits one to achieve excellent minimum sensitivity and performance.

Figure 21:
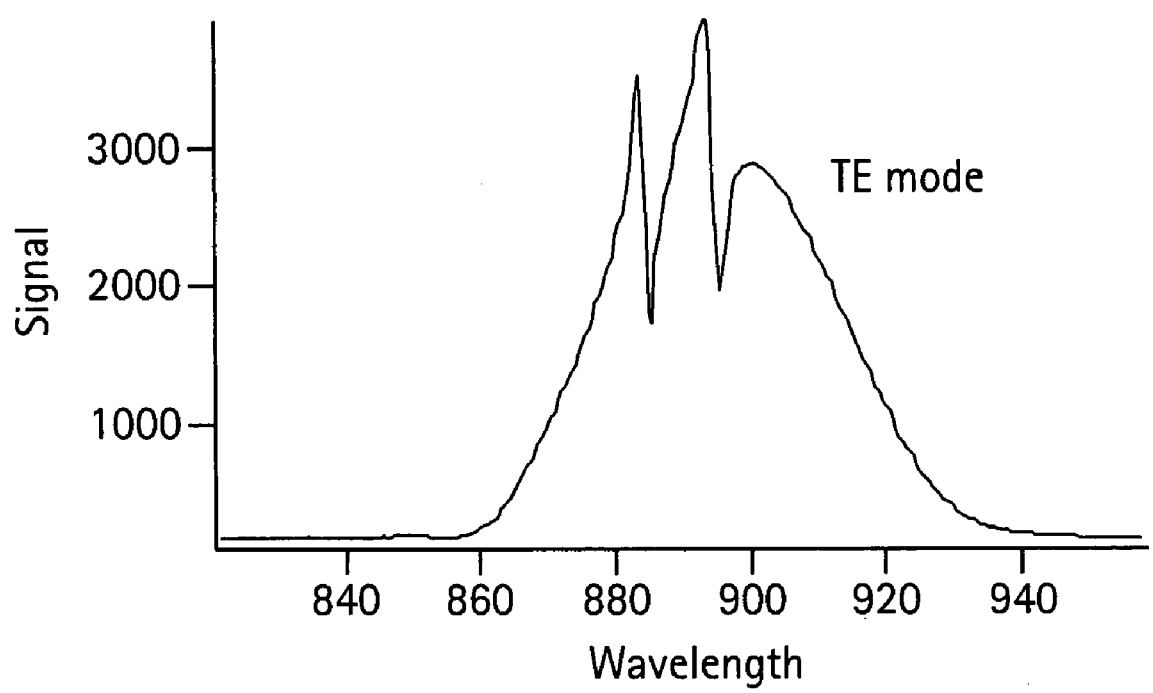
FIG. 21 represents an observed spectral double resonance. The two peaks at about 883 and 893 nm, separated by about 10 nm, are riding upon a large specular reflection background from a superluminescent diode source (~50 nm bandwidth).

The observation of the angular difference, or the spectral mean, allows one to create a reader system that more fully utilizes the resonant energy, has enhanced sensitivity, and has an increased robustness to specific forms of common mode noise. An example of this spectral double resonance is shown in FIG. 21. Just as in the angular case, one can analyze the system noise to show noise improvement from observing the mean wavelength signal. Table 2 presents a summary of the range and mean variance values in terms of pixels for both spectral peaks.

TABLE 2

| Variance of Peaks (pixels) | | |
|---|---|---|
| Lower | Upper | Mean |
| .0241 | .021 | .012 |

B. Environmental Insensitivity Improvement

Figure 22:
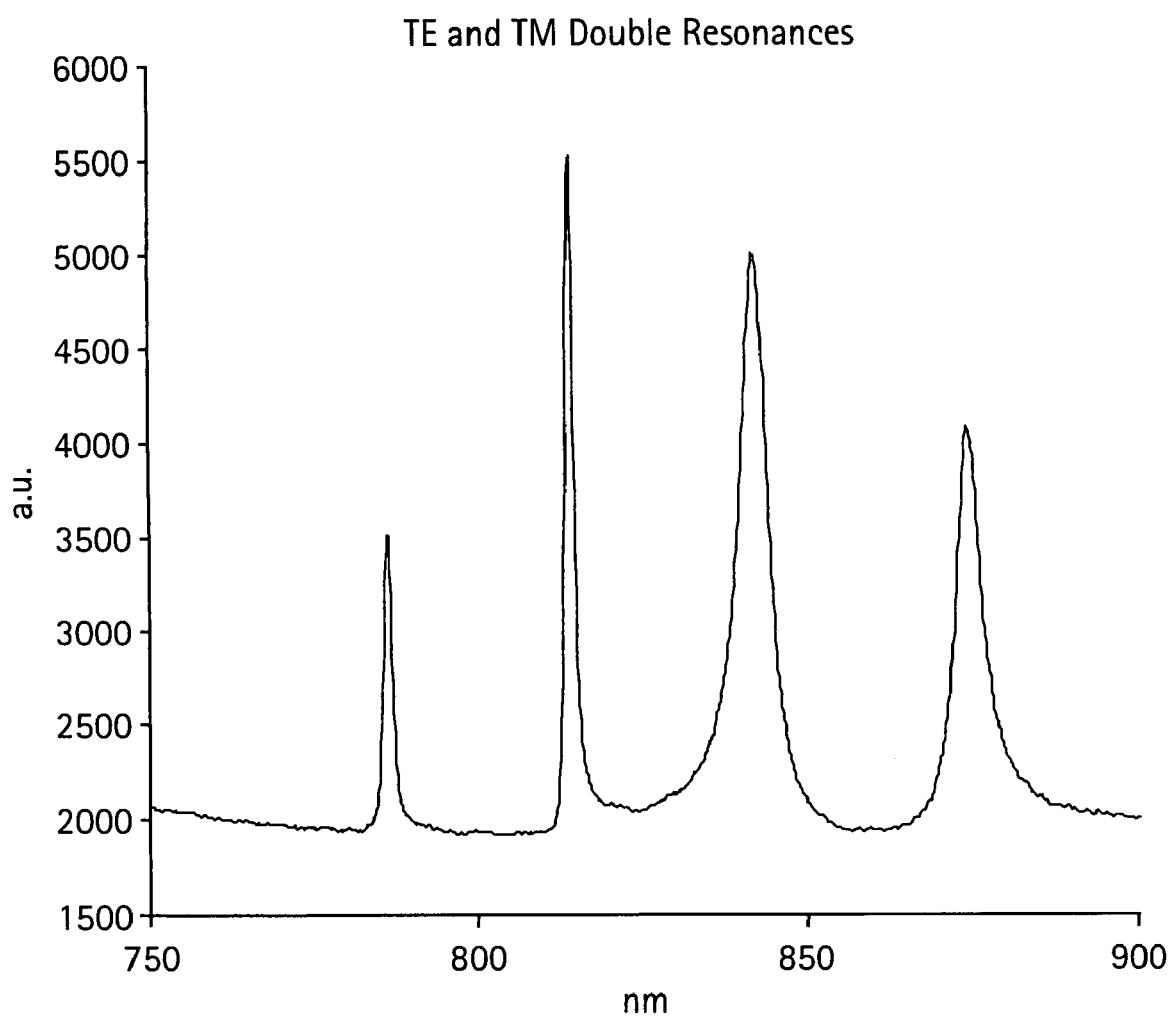
FIG. 22 shows the output of a GCW sensor interrogated with a broadband, white-light optical spectrum, used to investigate this GCW sensor's environmental stability against angular misalignment. The four peaks represent two sets of double resonances, one set each for TE (right) and TM (left) modes of the waveguide.
Figure 23:
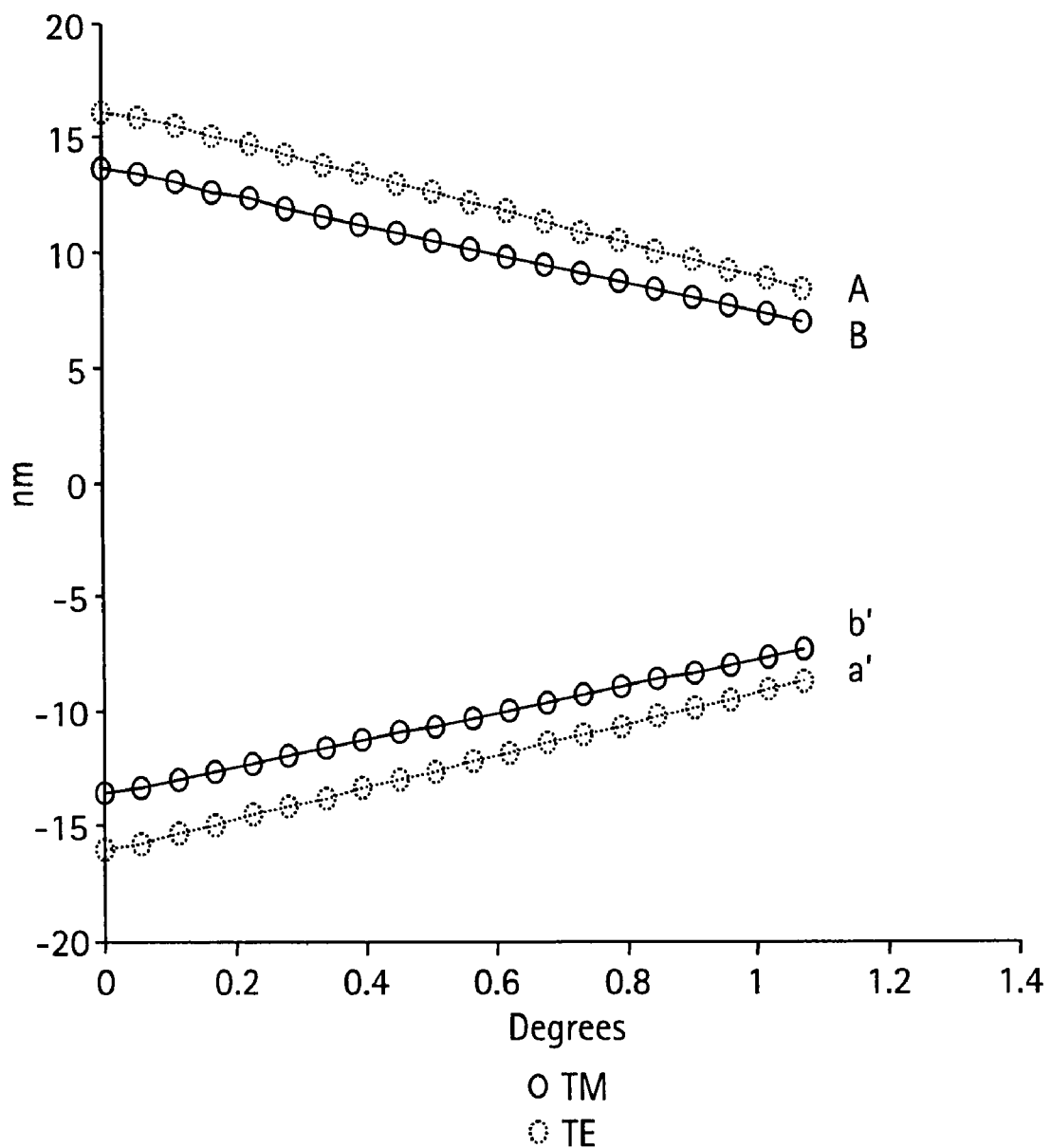
FIG. 23 shows the change or evolution of the spectral location of each resonance peak shown in FIG. 22, as the GCW sample is tilted relative to the input light beam. The outermost two curves (A, and a') represent the TE double resonances, while the innermost (B, top, and b', bottom) show the TM cases.

Using a very broadband spectral interrogation system, the reduction of environmental noise was tested, particularly the misalignment of the GCW sensor angle. FIG. 22 shows the two sets of double resonances (TM, two left; TE, two right) resulting from the sensor. As the plate was tilted, the location of each resonance was monitored, tracing out the curves of FIG. 23. This graph shows the susceptibility of GCW sensor systems to such misalignment: one degree of sensor tilt results in over 5 nm of resonance location change, whereas typical systems are capable of 0.1 pm resolution! A one-degree tilt therefore exceeds the required system noise limit by a factor of 50,000.

Figure 24:
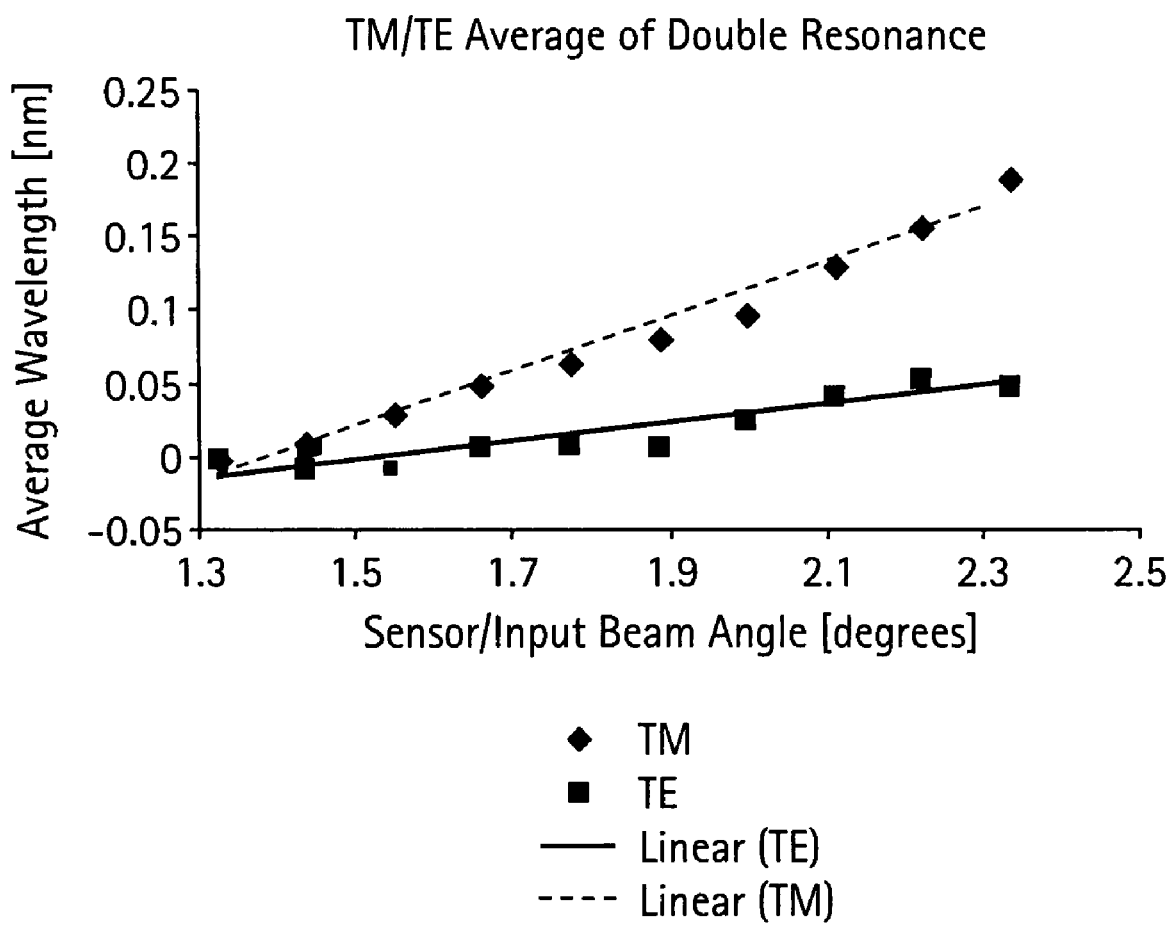
FIG. 24 is a graph showing the experimental average resonance under spectral interrogation scheme as a function of angle. Note that the average resonance location is not constant as would be expected from simple theory. The dispersion of the waveguide must be taken into account to explain the deviation.

Using the methodology of the double resonance, the two TE (or TM) resonance positions were subtracted from each other to correct this angular misalignment. FIG. 24 shows the result of this calculation, resulting in a factor of 50 reduction of the spectral deviation of the observable parameter for a one degree misalignment. If the misalignment were entirely corrected, these curves would be horizontal lines, unwavering with angular detuning. The downward trend of the graphs however indicates the presence of the dispersion term indicated by Equation [15] for the spectral system. In order to flatten these curves to an acceptable level (for this particular sensor), the dispersive term should be accounted for in this measurement.

C. Dispersion Correction Comparison

As discussed in Section II, Part B above, the double resonance scheme can be used to make the system insensitive to environmental perturbations, but under the spectral interrogation scheme one should take waveguide dispersion into account for accurate compensation. The data from FIG. 24 clearly supports this conclusion.

From FIG. 24, we can calculate the slope of the average resonance curves and compare with the theory of Section II, Part B. For the TE mode, the experimental slope is ~64 pm/degree while for the TM mode the slope is ~184 pm/degree. While these values are somewhat higher than the predictions above, it is expected that the experimental system added some offset to the values. For example, the GRIN lenses used to deliver the light from the optical fiber source to the GCW sensor are known to have some chromatic aberration that causes similar shifts of resonance wavelength as angle is varied. On the whole, the experimental data above supports the theory quite well, especially with respect to the zero-shift at zero-angle feature, as well as the factor of ~2.8 difference in slopes between the TE and TM curves.

In summary, the double resonance technique appears to be useful for both angular and spectral interrogation of resonant waveguide gratings sensors. The present invention has been described both in general and in detail by way of examples. Persons skilled in the art will understand that the invention is not limited necessarily to the specific embodiments disclosed. Modifications and variations may be made without departing from the scope of the invention as defined by the following claims or their equivalents, including equivalent components presently known, or to be developed, which may be used within the scope of the present invention. Hence, unless changes otherwise depart from the scope of the invention, the changes should be construed as being included herein.

We claim:

1. A method for interrogating a sensor, said method comprising the steps of:
   emitting a single light beam towards said sensor, where said emitted single light beam has enough angular/wavelength spread to simultaneously excite a forward propagating direction and a backward propagating direction within a waveguide of said sensor;
   receiving a single light beam from said sensor, where said received single light beam has a positive resonance and a negative resonance for a given superstrate refractive index on said sensor; and
   using both the positive resonance and the negative resonance within the received single light beam to obtain a signal which is used to indicate whether or not a biological or chemical agent is located on said sensor.

2. The method of claim 1, wherein said emitting step is performed by emitting the single light beam at a substantially normal incidence towards said sensor.

3. The method of claim 1, wherein said receiving step is performed by using a single detector to receive the single light beam which is out-coupled from said sensor.

4. The method of claim 1, wherein when said emitting step and said receiving step are performed using an angular interrogation system then said using step is performed by determining a difference between the positive resonance and the negative resonance to obtain the signal which indicates whether or not the biological or chemical agent is located on said sensor.

5. The method of claim 1, wherein when said emitting step and said receiving step are performed using a spectral interrogation system then said using step is performed by determining a mean between the positive resonance and the negative resonance to obtain the signal which indicates whether or not the biological or chemical agent is located on said sensor.

6. The method of claim 5, wherein when said emitting step and said receiving step are performed using the spectral interrogation system then said using step further includes a step of compensating for dispersion of the waveguide in said sensor in addition to determining the mean between the positive resonance and the negative resonance to obtain the signal which indicates whether or not the biological or chemical agent is located on the surface of said sensor.

7. A method for interrogating a sensor, said method comprising the steps of:
   providing the sensor which has a evanescent-field sensing region comprising a substrate surface having at least a bio- or chemo-responsive layer;
   exposing the sensing region to an analyte;
   emitting a single light beam towards said sensor to generate a double resonance by exciting a forward propagating direction and a backward propagating direction within a waveguide of said sensor;
   receiving a single light beam containing the double resonance out-coupled from said sensor; and
   using the double resonance within the received single light beam to obtain a signal which is used to monitor a response from said sensor.

8. The method of claim 7, wherein said signal is obtained by measuring an angular shift using both of the resonances which effectively doubles an interrogation sensitivity of said sensor when compared to using an angular shift that was measured by using one of the resonances.

9. The method of claim 7, wherein said signal is obtained by measuring a spectral shift using both of the resonances which effectively improves an observed signal-to-noise ratio of said sensor by a factor of at least about $\sqrt{2}$ when compared to measuring a spectral shift using one of the resonances.

10. The method of claim 7, wherein said signal based on the double resonances is substantially insensitive to environmental perturbations.

11. The method of claim 7, wherein said signal based on the double resonances is substantially insensitive to an angular position of said sensor.

12. The method of claim 7, wherein said signal based on the double resonances, together with a mathematical correction to account for dispersion of the waveguide in said sensor, is substantially insensitive to an angular position of said sensor.

* * * * *